United States Patent
Barlaam et al.

(10) Patent No.: US 7,718,653 B2
(45) Date of Patent: May 18, 2010

(54) PYRIMIDINE DERIVATIVES FOR INHIBITING EPH RECEPTORS

(75) Inventors: Bernard Christophe Barlaam, Reims (FR); Richard Ducray, Reims (FR); Jason Grant Kettle, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/174,339

(22) Filed: Jul. 16, 2008

(65) Prior Publication Data

US 2009/0023719 A1 Jan. 22, 2009

(30) Foreign Application Priority Data

Jul. 16, 2007 (EP) .................. 07301236

(51) Int. Cl.
- *A61K 31/5355* (2006.01)
- *A61K 31/496* (2006.01)
- *C07D 265/30* (2006.01)
- *C07D 413/14* (2006.01)
- *C07D 403/14* (2006.01)

(52) U.S. Cl. .............. 514/232.5; 514/233.8; 514/234.5; 514/252.2; 544/79; 544/80; 544/122; 544/295

(58) Field of Classification Search ........................ None
See application file for complete search history.

(56) References Cited

U.S. PATENT DOCUMENTS

| | | | |
|---|---|---|---|
| 2006/0148800 A1 | 7/2006 | Stadtmueller et al. | |
| 2008/0242663 A1 | 10/2008 | Ashton et al. | |

FOREIGN PATENT DOCUMENTS

| | | | |
|---|---|---|---|
| WO | 03/074514 A1 | 9/2003 | |
| WO | 2004080980 A1 | 9/2004 | |
| WO | 2005016894 A1 | 2/2005 | |
| WO | 2006021454 A2 | 3/2006 | |
| WO | 2006021544 A1 | 3/2006 | |
| WO | 2006101977 A2 | 9/2006 | |
| WO | 2006129100 A1 | 12/2006 | |
| WO | 2007009681 A1 | 1/2007 | |
| WO | 2007028445 A1 | 3/2007 | |
| WO | 2007035309 A1 | 3/2007 | |
| WO | 2007085540 A1 | 8/2007 | |
| WO | 2007085833 A2 | 8/2007 | |
| WO | WO 2008/118822 | * | 10/2008 |
| WO | 2008132505 A1 | 11/2008 | |

OTHER PUBLICATIONS

Chen et al. "Eph Receptors and Ephrins in Cancer: Common Themes and Controversies." Cancer Res 2008, 68 (24). Dec. 15, 2008.*
Golub et al. "Molecular Classification of Cancer: Class Discovery and Class Prediction by Gene Expression Monitoring." Science (1999), vol. 286, 521-537.*
Lala et al. "Role of nitric oxide in tumor progression: Lessons from experimental tumors." Cancer and Metastasis Reviews (1998), 17(1), 91-106.*
"Cancer." MedLine Plus. (2009). Accessed Mar. 17, 2009. <http://www.nlm.nih.gov/medlineplus/cancer.html>.*
Patani et al. "Bioisosterism: A Rational Approach in Drug Design." Chem Rev. 1996, 96, 3147-3176.*
Bamborough, Paul; Bioorganic & Medicinal Chemistry Letters; 17; 2007; 4363-4368.
Bardelle, Catherine; Bioorganic & Medicinal Chemistry Letters; 18; 2008; 2776-2780.
Bardelle, Catherine; Bioorganic & Medicinal Chemistry Letters; 18; 2008; 5717-5721.

* cited by examiner

*Primary Examiner*—Rei-Tsang Shiao
*Assistant Examiner*—Alicia L Fierro

(57) ABSTRACT

A compound of formula (I)

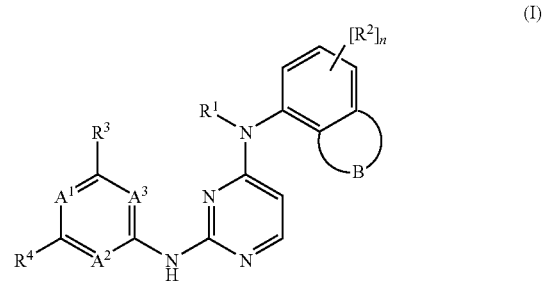

where one of $A^1$, $A^2$ or $A^3$ is N, and the others are independently selected from CH or N; ring B is a fused 5 or 6-membered carbocyclic or heterocyclic ring which is optionally substituted as defined in the specification, and $R^1$, $R^2$, $R^3$, $R^4$, and n are as defined in the specification.

The compounds are inhibitors of EphB4 or EphA2 and therefore may be useful in pharmaceutical compositions for the treatment of conditions such as cancer.

14 Claims, No Drawings

PYRIMIDINE DERIVATIVES FOR INHIBITING EPH RECEPTORS

This application claims the benefit under 35 U.S.C. §119 (a)-(d) of Application No. 07301236.1 (EP) filed on 16 Jul. 2007.

The present invention relates to novel pyrimidine derivatives, to pharmaceutical compositions containing these derivatives and to their use in therapy, in particular in the prevention and treatment of solid tumour disease in a warm blooded animal such as man.

Many of the current treatment regimes for cell proliferation diseases such as psoriasis and cancer utilize compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.* 1988, 57, 443; Larsen et al., *Ann. Reports in Med. Chem.*, 1989, Chpt. 13).

The first group of tyrosine kinases to be identified arose from such viral oncogenes, for example pp60$^{v-Src}$ tyrosine kinase (otherwise known as v-Src), and the corresponding tyrosine kinases in normal cells, for example pp60$^{c-Src}$ tyrosine kinase (otherwise known as c-Src).

Receptor tyrosine kinases are important in the transmission of biochemical signals which initiate a variety of cell responses including proliferation, survival and migration. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research* 1993, 60 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGF1 receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

The Eph family is the largest known family of receptor tyrosine kinses, with 14 receptors and 8 cognate ephrin ligands identified in mammals (Reviewed in Kullander and Klein, *Nature Reviews Molecular Cell Biology*, 2002, 3, 475-486). The receptor family is further sub-divided into two sub-families defined largely by homology of extracellular domains and affinity towards ligand type. In general, all Ephs contain an intracellular tyrosine kinase domain and an extracellular Ig-like domain with a cysteine-rich region with 19 conserved cysteines and two fibronectin type III domains. The A-class of Ephs consists of 8 receptors termed EphA1-8, which generally bind to their cognate ephrinA class of ligands termed ephrinA1-5. The B-class consistents of 6 receptors termed EphB1-6, which bind to their cognate ephrinB ligands termed ephrinB1-3. Eph receptor ligands are unusual and differ to most other receptor tyrosine kinase ligands in that they are also tethered to cells, via a glycosylphosphatidylinositol linker in ephrinA ligands or an integral transmembrane region in ephrinB ligands. Binding of ephrin ligand to the Eph partner induces a conformational change within the Eph intracellular domain that enables phosphorylation of tyrosine residues within an auto-inhibitory juxtamembrane region, which relieves this inhibition of catalytic site and enables additional phosphorylation to stabilize the active conformation and generate more docking sites for downstream signaling effectors.

Furthermore, evidence indicates that Eph/ephrin signaling can regulate other cell responses such as proliferation and survival.

There is growing evidence that Eph receptor signaling may contribute to tumourigenesis in a wide variety of human cancers, either on tumour cells directly or indirectly via modulation of vascularization. For instance, many Eph receptors are over-expressed in various tumour types (Reviewed in Surawska et al., *Cytokine & Growth Factor Reviews*, 2004, 15, 419-433, Nakamoto and Bergemann, *Microscopy Res and Technique*, 2002, 59, 58-67); EphA2 and other EphA receptor levels are elevated in diverse tumours such as leukemias, breast, liver, lung, ovarian and prostate. Similarly expression of EphB receptors including EphB4 is up-regulated in tumours such as neuroblastomas, leukemias, breast, liver, lung and colon. Moreover, various in vitro and in vivo studies particularly regarding EphA2 and EphB4 have indicated that over-expression of Eph receptors on cancer cells is able to confer tumourigenic phenotypes such as proliferation and invasion, consistent with the speculated role in oncogenesis.

For instance, inhibition of EphB4 expression using interfering-RNA or antisense oligodeoxynucleotides inhibited proliferation, survival and invasion of PC3 prostate cancer cells in vitro and in vivo xenograft model (Xia et al., *Cancer Res.*, 2005, 65, 4623-4632). EphA2 over-expression in MCF-10A mammary epithelial cells is sufficient to cause tumourigenesis (Zelinski et al., *Cancer Res.*, 2001, 61, 2301-2306). Inhibition of EphA2 function with therapeutic antibodies (Coffman et al., *Cancer Res.*, 2003, 63, 7907-7912) or interfering-RNA (Landen et al., *Cancer Res.*, 2005, 15, 6910-6918) has been demonstrated to inhibit tumour growth in in vivo xenograft models. Expression of kinase-dead EphA2 mutant receptors in breast cancer cell lines inhibited growth and metasis of xenograft tumours in vivo, consistent with an essential role of the kinase domain (Fang et al., *Oncogene*, 2005, 24, 7859-7868).

In addition to compelling role of Eph receptors on tumour cells, there is good evidence that both EphA2 and EphB4 may contribute to tumour vascularisation (Reviewed in Brantley-Sieders et al., *Current Pharmaceutical Design*, 2004, 10, 3431-3442, Cheng et al., *Cytokine and Growth Factor Reviews*, 2002, 13, 75-85). Members of Eph family including both EphA2 and EphB4 are expressed on endothelial cells. Transgenic studies have shown that disruption of EphB4 (Gerety et al., *Molecular Cell*, 1999, 4, 403-414) or its ligand ephrinB2 (Wang et al., *Cell*, 1998, 93, 741-753) causes embryonic lethality associated with vascular modeling defects consistent with a critical role in vessel development.

EphB4 activation stimulates endothelial cell proliferation and migration in vitro (Steinle et al., *J. Biol. Chem.*, 2002, 277, 43830-43835).

Moreover, inhibition of EphB4 signaling using soluble extracellular-domains of EphB4 have been shown to inhibit tumour growth and anagiogenesis in in vivo xenograft studies (Martiny-Baron et al., Neoplasia, 2004, 6, 248-257, Kertesz et al., *Blood*, 2005, Pre-published online). Similarly, soluble EphA2 inhibited tumour vascularisation in a variety of in vivo models (Brantley et al., *Oncogene*, 2002, 21, 7011-7026, Cheng et al., *Neoplasia*, 2003, 5, 445-456).

Accordingly it has been recognized that an inhibitor of Eph receptors, particularly EphB4 or EphA2, should be of value as a selective inhibitor of the proliferation and survival of tumour cells either targeted at tumour cells directly or via effects on tumour vascularisation. Thus, such inhibitors should be valuable therapeutic agents for the containment and/or treatment of tumour disease.

The applicants have found that certain pyrimidines are useful in the inhibition of EphB4 or EphA2 and therefore may be useful in therapy, where such enzymes are implicated.

According to the present invention, there is provided a compound of formula (I)

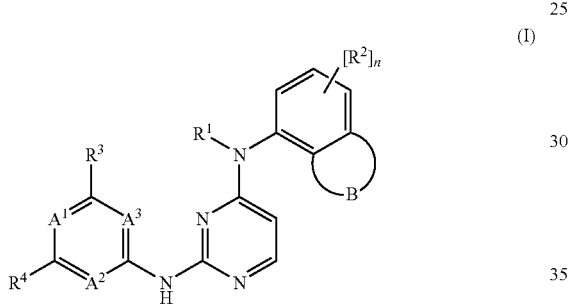

wherein at least one of $A^1$, $A^2$ or $A^3$ is N, and the others are independently selected from CH or N;

$R^1$ is hydrogen or a (1-4C)alkyl group which is optionally substituted by one or more substituent groups selected from —$OR^5$ (wherein $R^5$ is selected from hydrogen or (1-2C)alkyl), cyano, halo, or —$NR^6R^7$ (where $R^6$ and $R^7$ are independently selected from hydrogen, (1-2C)alkyl or (1-2C)alkanoyl);

ring B is a fused 5 or 6-membered carbocyclic or heterocyclic ring which is optionally substituted on a carbon atom by one or more halo groups or $C_{1-6}$alkyl groups, and where any nitrogen atoms in the ring are optionally substituted by a $C_{1-6}$alkyl or $C_{1-6}$alkylcarbonyl;

n is 0, 1, 2 or 3, and each group $R^2$ is independently selected from halogeno, trifluoromethyl, cyano, nitro or a group of sub-formula (i):

 (i)

where $X^1$ is selected from a direct bond or O, S, SO, $SO_2$, $OSO_2$, $NR^{13}$, CO, CH($OR^{13}$), $CONR^{13}$, $N(R^{13})CO$, $SO_2N(R^{13})$, $N(R^{13})SO_2$, $C(R^{13})_2O$, $C(R^{13})_2S$, $C(R^{13})_2N(R^{13})$ and $N(R^{13})C(R^{13})_2$, wherein $R^{13}$ is hydrogen or $C_{1-6}$alkyl and $R^{11}$ is selected from hydrogen, $C_{1-6}$ alkyl, $C_{2-8}$alkenyl, $C_{2-8}$alkynyl, $C_{3-8}$cycloalkyl, aryl or heterocyclyl, $C_{1-6}$ alkyl$C_{3-8}$cycloalkyl, $C_{1-6}$ alkylaryl or $C_{1-6}$ alkylheterocyclyl, any of which may be optionally substituted with one or more groups selected from halogeno, trifluoromethyl, cyano, nitro, hydroxy, amino, carboxy, carbamoyl, $C_{1-6}$alkoxy, $C_{2-6}$alkenyoxyl, $C_{2-6}$alkynyloxy, $C_{1-6}$alkylthio, $C_{1-6}$alkylsulphinyl, $C_{1-6}$alkylsulphonyl, $C_{1-16}$alkylamino, di-($C_{1-16}$alkyl)amino, $C_{1-16}$alkoxycarbonyl, N—$C_{1-6}$alkylcarbamoyl, N,N-di-($C_{1-6}$alkyl)carbamoyl, $C_{2-6}$alkanoyl, $C_{2-6}$alkanoyloxy, $C_{2-6}$alkanoylamino, N—$C_{1-6}$alkyl-$C_{2-6}$alkanoylamino, $C_{3-6}$alkenoylamino, N—$C_{1-6}$alkyl-$C_{3-6}$alkenoylamino, $C_{3-6}$alkynoylamino, N—$C_{1-6}$alkyl-$C_{3-6}$alkynoylamino, N—$C_{1-6}$alkylsulphamoyl, N,N-di-($C_{1-6}$alkyl)sulphamoyl, $C_{1-6}$alkanesulphonylamino and N—$C_{1-6}$alkyl-$C_{1-6}$alkanesulphonylamino, any heterocyclyl group within $R^{11}$ optionally bears 1 or 2 oxo or thioxo substituents;

$R^3$ is selected from:
 (i) hydrogen, halo, nitro, cyano, or hydroxy;
 (ii) an optionally substituted (1-6C)alkyl, (2-6C)alkenyl, or (2-6C)alkynyl group wherein the optional substituents are selected from: cyano; halo;
  a group of sub-formula:

—W—$R^9$ wherein W is selected from —O—, —S(O)$_p$— (where p is 0, 1 or 2), —CO—, —$NR^bCO$—, —$CONR^b$—, —$NR^bCONR^b$—, —$SO_2NR^b$—, —$NR^bSO_2$—, or —$NR^bCOO$—;

$R^b$ is selected from hydrogen or (1-2C)alkyl;
  and $R^9$ is selected from hydrogen or (1-4C)alkyl;
  or —$NR^{10}R^{10a}$, where $R^{10}$ and $R^{10a}$ are independently selected from hydrogen, or (1-2C)alkyl, or $R^{10}$ and $R^{10a}$ are linked to form a 4, 5, 6 or 7 membered heterocyclic ring which optionally comprises, in addition to the nitrogen atom to which $R^{10}$ and $R^{10a}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C)alkyl, hydroxy(1-4C)alkyl, (1-2C)alkoxy-(1-4C)alkyl, or (1-4C)alkanoyl;
 (iii) a group —$NR^{12}R^{12a}$, wherein $R^{12}$ and $R^{12a}$ are each independently selected from hydrogen or (1-6C)alkyl, or $R^{12}$ and $R^{12a}$ are linked to form a 4, 5, 6 or 7-membered heterocyclic ring which optionally comprises, in addition to the nitrogen atom to which $R^{12}$ and $R^{12a}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C)alkyl, hydroxy(1-4C)alkyl, (1-2C)alkoxy-(1-4C)alkyl, or (1-4C)alkanoyl;
 (iv) a group of formula (II):

wherein X is selected from —O—, —S(O)$_p$— (where p is 0, 1 or 2), —CO—, —$NR^cCO$—, —$CONR^c$—, —$NR^cCOO$—, and —$NR^cSO_2$—,
  where $R^c$ is selected hydrogen or (1-2C)alkyl;

$R^{14}$ is a (1-4C)alkyl group which is optionally substituted by halo, hydroxy, cyano, (1-4C)alkoxy, or $R^{14}$ is $NR^{15}R^{16}$ where $R^{15}$ and $R^{16}$ are independently selected from hydrogen, (1-2C)alkanoyl or (1-2C)alkyl, or $R^{15}$ and $R^{16}$ are linked to form a 4, 5, 6 or 7-membered heterocyclic ring which optionally comprises, in addition to the nitrogen atom to which $R^{15}$ and $R^{16}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom is optionally substituted by (1-4C)alkyl, hydroxy(1-4C)alkyl, (1-2C)alkoxy-(1-4C)alkyl, or (1-4C)alkanoyl; or (v) a 4-7 membered heterocyclic group which is linked via a carbon atom; and $R^4$ is a group —$NR^{17}R^{18}$, wherein $R^{17}$ and $R^{18}$ are linked to form a 4, 5, 6 or 7 membered heterocyclic ring which optionally comprises, in addition to the nitrogen atom to which $R^{17}$ and $R^{18}$ are attached, one or two further heteroatoms selected from O, N or S, and wherein any S atoms that are present may be optionally oxidised to form an SO or $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C) alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C) alkyl, hydroxy(1-4C)alkyl, (1-2C)alkoxy-(1-4C)alkyl, or (1-4C)alkanoyl; or a pharmaceutically acceptable salt thereof.

In this specification the generic term "alkyl" includes both straight-chain and branched-chain alkyl groups such as propyl, isopropyl and tert-butyl. However references to individual alkyl groups such as "propyl" are specific for the straight-chain version only, references to individual branched-chain alkyl groups such as "isopropyl" are specific for the branched-chain version only. An analogous convention applies to other generic terms, for example (1-6C)alkoxy includes methoxy, ethoxy and isopropoxy, (1-6C)alkylamino includes methylamino, isopropylamino and ethylamino, and di-[(1-6Calkyl]amino includes dimethylamino, diethylamino and N-methyl-N-isopropylamino. Similarly alkenyl or alkynyl groups may be straight chain or branched.

The term "aryl" refers to phenyl or naphthyl, particularly phenyl.

The term "halogen" or "halogeno" includes fluoro, chloro, bromo, or iodo.

The term "heterocyclyl" or "heterocyclic" refers to saturated, partially saturated or unsaturated, mono, bicyclic or tricyclic rings containing 3-15 atoms, of which at least one atom is chosen from nitrogen, sulphur or oxygen. These groups may, unless otherwise specified, be carbon or nitrogen linked. In addition, or a ring sulphur atom may be optionally oxidised to form the S-oxides. More particularly a "heterocyclyl" is a saturated, partially saturated or unsaturated, mono or bicyclic ring containing 3-12 atoms. Monocyclic rings suitably contain from 3-7 ring atoms, in particular 5 or 6 ring atoms.

Examples and suitable values of the term "heterocyclyl" are thienyl, piperidinyl, morpholinyl, furyl, thiazolyl, pyridyl, imidazolyl, 1,2,4-triazolyl, thiomorpholinyl, coumarinyl, pyrimidinyl, phthalidyl, pyrazolyl, pyrazinyl, pyridazinyl, benzothienyl, benzimidazolyl, tetrahydrofuryl, [1,2,4]triazolo[4,3-a]pyrimidinyl, piperidinyl, indolyl, 1,3-benzodioxolyl and pyrrolidinyl, pyrrolyl, quinolinyl, isoquinolinyl, isoxazolyl, benzofuranyl, 1,2,3-thiadiazolyl, 1,2,5-thiadiazolyl, pyrimidinyl, 2,1-benzisoxazolyl, 4,5,6,7-tetrahydro-2H-indazolyl, imidazo[2,1-b][1,3]thiazolyl, tetrahydrofuranyl, tetrahydropyranyl, piperidinyl, morpholinyl, 2,3-dihydro-1-benzofuryl, 2,3-dihydro-1,4-benzodioxinyl, 1,3-benzothiazolyl, 3,4-dihydro-2H-benzodioxepinyl, 2,3-dihydro-1,4-benzodioxinyl, chromanyl, 2,3-dihydrobenzofuranyl, imidazo[2,1-b][1,3]thiazolyl, isoindolinyl, oxazolyl, pyridazinyl, quinoxalinyl, tetrahydrofuryl, 4,5,6,7-tetrahydro-1-benzofuryl, 4,5,6,7-tetrahydro-2H-indazolyl, 4,5,6,7-tetrahydro-1H-indolyl, tetrahydropyranyl or 1,2,3,4-tetrahydroquinolinyl.

Heterocyclyl groups may be non-aromatic or aromatic in nature. Aromatic heterocyclyl groups are referred to as heteroaryl. Heteroaryl groups are totally unsaturated, mono or bicyclic rings containing 3-12 atoms of which at least one atom is chosen from nitrogen, sulphur or oxygen, which may, unless otherwise specified, be carbon or nitrogen linked. Suitably "heteroaryl" refers to a totally unsaturated, monocyclic ring containing 5 or 6 atoms or a bicyclic ring containing 8-10 atoms of which at least one atom is chosen from nitrogen, sulphur or oxygen, which may, unless otherwise specified, be carbon or nitrogen linked. Examples and suitable values of the term "heteroaryl" are thienyl, furyl, thiazolyl, pyrazolyl, isoxazolyl, imidazolyl, pyrrolyl, thiadiazolyl, isothiazolyl, triazolyl, pyranyl, indolyl, pyrimidyl, pyrazinyl, pyridazinyl, benzothienyl, pyridyl and quinolyl.

Particular novel compounds of the invention include, for example, compounds of Formula I, or pharmaceutically-acceptable salts thereof, wherein, unless otherwise stated, each of $R^1$, n, $R^2$, $R^3$, $R^4$, $A^1$, $A^2$, $A^3$ or B has any of the meanings defined hereinbefore or in paragraphs (1) to (45) hereinafter:—

(1) $R^1$ is (1-4C)alkyl;
(2) $R^1$ is selected from hydrogen, methyl, ethyl, propyl, isopropyl, 2-methylpropyl or cyclopropylmethyl;
(3) $R^1$ is selected from hydrogen, methyl, ethyl, isopropyl or cyclopropylmethyl;
(4) $R^1$ is methyl;
(5) $R^1$ is isopropyl;
(6) $R^1$ is cyclopropylmethyl;
(7) $R^1$ is ethyl;
(8) $R^1$ is hydrogen;
(9) n is 0, 1 or 2;
(10) n is 0 or 1;
(11) n is 0;
(12) n is 1;
(13) each $R^2$ group present is independently selected from halogeno, trifluoromethyl, cyano, hydroxy, $C_{1-6}$alkyl, $C_{2-8}$alkenyl, $C_{2-8}$alkynyl and $C_{1-6}$alkoxy;
(14) each $R^2$ group present is independently selected from chloro, fluoro, bromo, trifluoromethyl, cyano, hydroxy, methyl, ethyl, ethynyl, methoxy and ethoxy;
(15) each $R^2$ group present is halogeno,
(16) each $R^2$ group present is selected from bromo, chloro or fluoro.
(17) each $R^2$ group present is chloro,

(18) $R^3$ is selected from:
  (i) hydrogen, halo, nitro, cyano, or hydroxy;
  (ii) an optionally substituted (1-6C)alkyl group, wherein the optional substituents are selected from cyano, halo, or a group of sub-formula:

—W—$R^9$ wherein W is selected from —O—, —S(O)$_p$— (where p is 0, 1 or 2), —CO—, —NR$^b$CO—, or —CONR$^b$—;
  $R^b$ is selected from hydrogen or (1-2C)alkyl;
  and $R^9$ is selected from hydrogen or (1-4C)alkyl;
  or —NR$^{10}$R$^{10a}$ where $R^{10}$ and $R^{10a}$ are independently selected from hydrogen, (1-2C)alkanoyl or (1-2C)alkyl, or $R^{10}$ and $R^{10a}$ are linked to form a 5, or 6 membered heterocyclic ring which optionally comprises, in addition to the nitrogen atom to which $R^{10}$ and $R^{10a}$ are attached, one or two further heteroatoms selected from O, N or S, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom present in the ring is optionally substituted by (1-4C)alkyl or (1-4C)alkanoyl;
  (iii) a group —NR$^{12}$R$^{12a}$, wherein $R^{12}$ and $R^{12a}$ are each independently selected from hydrogen or (1-6C)alkyl, or $R^{12}$ and $R^{12a}$ are linked to form a 5, 6 or 7-membered heterocyclic ring which comprises, in addition to the nitrogen atom to which $R^{12}$ and $R^{12a}$ are attached, one or two further heteroatoms selected from O, N or S, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom present in the ring is optionally substituted by (1-4C)alkyl or (1-4C)alkanoyl; or
  (iv) a group of formula (II):

—X—$R^{14}$ wherein X is selected from —O—, —S(O)$_p$— (where p is 0, 1 or 2), —CO—, NR$^c$CO—, CONR$^c$, or NR$^c$COO—,
  where $R^c$ is selected hydrogen or (1-2C)alkyl;
  $R^{14}$ is a (1-4C)alkyl group which is optionally substituted by halo, hydroxy, cyano, (1-4C)alkoxy, or $R^{14}$ is

—NR$^{15}$R$^{16}$ where $R^{15}$ and $R^{16}$ are independently selected from hydrogen, (1-2C)alkanoyl or (1-2C)alkyl, or $R^{15}$ and $R^{16}$ are linked to form a 5, or 6-membered heterocyclic ring which optionally comprises, in addition to the nitrogen atom to which $R^{15}$ and $R^{16}$ are attached, one or two further heteroatoms selected from O, N or S, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom present in the ring is optionally substituted by (1-4C)alkyl or (1-4C)alkanoyl;

(19) $R^3$ is selected from:
  (i) hydrogen, halo, cyano, or hydroxy;
  (ii) an optionally substituted (1-4C)alkyl group wherein the optional substituents are selected from cyano, halo, a group of sub-formula:

—W—$R^9$ wherein W is selected from —O—, —S(O)$_p$— (where p is 0, 1 or 2), —CO—, —NR$^b$CO—, or —CONR$^b$—;
  $R^b$ is selected from hydrogen or (1-2C)alkyl and $R^9$ is selected from hydrogen or (1-4C)alkyl;
  or —NR$^{10}$R$^{10a}$, where $R^{10}$ and $R^{10a}$ are independently selected from hydrogen or (1-2C)alkyl, or $R^{10}$ and $R^{10a}$ are linked to form a 5 or 6 membered heterocyclic ring which optionally comprises, in addition to the nitrogen atom to which $R^{10}$ and $R^{10a}$ are attached, one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom present in the ring is optionally substituted by (1-4C)alkyl;
  (iii) a group —NR$^{12}$R$^{12a}$, wherein $R^{12}$ and $R^{12a}$ are each independently selected from hydrogen or (1-6C)alkyl, or $R^{12}$ and $R^{12a}$ are linked to form a 5, 6 or 7-membered heterocyclic ring, and wherein, in addition to the nitrogen atom to which $R^{12}$ and $R^{12a}$ are attached, the ring optionally comprises one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom present in the ring is optionally substituted by (1-4C)alkyl; or
  (iv) a group of formula (II):

—X—$R^{14}$ wherein X is selected from —O—, —S(O)$_p$— (where p is 0, 1 or 2), or —CONR$^c$—,
  where $R^c$ is selected hydrogen or (1-2C)alkyl;
  $R^{14}$ is a (1-4C)alkyl group which is optionally substituted by halo, hydroxy, cyano, (1-4C)alkoxy;

(20) $R^3$ is selected from:
  (i) hydrogen, halo, or cyano;
  (ii) an optionally substituted (1-2C)alkyl group wherein the optional substituents are selected from cyano, halo, a group of sub-formula:

—W—$R^9$ wherein W is selected from —O—, —S(O)$_p$— (where p is 0, 1 or 2), —CO—, —NR$^b$CO—, or —CONR$^b$—;
  $R^b$ is selected from hydrogen or (1-2C)alkyl and $R^9$ is selected from hydrogen or (1-4C)alkyl;
  or —NR$^{10}$R$^{10a}$, where $R^{10}$ and $R^{10a}$ are independently selected from hydrogen or (1-2C)alkyl), or $R^{10}$ and $R^{11}$ are linked to form a 5 or 6 membered heterocyclic ring which optionally comprises, in addition to the nitrogen atom to which $R^{10}$ and $R^{11}$ are attached, one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom present in the ring is optionally substituted by (1-4C)alkyl;
  (iii) a group —NR$^{12}$R$^{13}$, wherein $R^{12}$ and $R^{13}$ are each independently selected from hydrogen or (1-6C)alkyl, or $R^{12}$ and $R^{13}$ are linked to form a 5, 6 or 7-membered heterocyclic ring, and wherein, in addition to the nitrogen atom to which $R^{12}$ and $R^{13}$ are attached, the ring optionally comprises one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom present in the ring is optionally substituted by (1-4C)alkyl; or (iv) a group of formula (II):

—X—R$^{14}$ wherein X is selected from —O—, —S(O)$_p$— (where p is 0, 1 or 2), or —CONR$^c$—,
where R$^c$ is selected hydrogen or (1-2C)alkyl;
R$^{14}$ is a (1-4C)alkyl group which is optionally substituted by halo, hydroxy, cyano, (1-4C)alkoxy;

(21) R$^3$ is a group —NR$^{12}$R$^{12a}$, wherein R$^{12}$ and R$^{12a}$ are each independently selected from hydrogen or (1-6C)alkyl, or R$^{12}$ and R$^{12a}$ are linked to form a 5, 6 or 7-membered heterocyclic ring, and wherein, in addition to the nitrogen atom to which R$^{12}$ and R$^{12a}$ are attached, the ring optionally comprises one or two further heteroatoms selected from O, N or S, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom present in the ring is optionally substituted by (1-4C)alkyl or (1-4C)alkanoyl;

(22) R$^3$ is a group —NR$^{12}$R$^{12a}$ where R$^{12}$ and R$^{12a}$ are linked to form a 6 membered heterocyclic ring which optionally comprises, in addition to the nitrogen atom to which R$^{12}$ and R$^{12a}$ are attached, one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom is optionally substituted by (1-4C)alkyl, hydroxy(1-4C)alkyl or (1-4C)alkanoyl;

(23) R$^3$ is a group of formula:

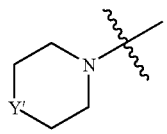

wherein Y' is selected from O, S, NR$^{y'}$, or CR$^{z'}$, where R$^{y'}$ is selected from hydrogen, (1-2C)alkyl, hydroxy(1-2C)alkyl, (1-2C)alkoxy(1-2C)alkyl, or (1-2C)alkanoyl, and R$^{z'}$ is selected from hydrogen, hydroxy, (1-2C)alkyl, hydroxy(1-2C)alkyl, (1-2C)alkoxy(1-2C)alkyl, or (1-2C)alkanoyl;

(24) R$^3$ is a group of formula:

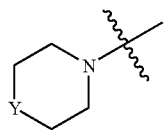

wherein Y' is selected from O, NR$^{y'}$, or CR$^{z'}$, where R$^{y'}$ is selected from hydrogen or (1-2C)alkyl, and R$^{z'}$ is selected from hydrogen or hydroxy;

(25) R$^3$ is selected from morpholin-4-yl, 4-methylpiperazin-1-yl, or 4-hydroxypiperidin-1-yl;

(26) R$^3$ is morpholin-4-yl;

(27) R$^3$ is halo such as chloro;

(28) R$^3$ is a 4-7 membered heterocyclic group which is linked via a carbon atom;

(29) R$^3$ is a 5-6 membered heterocyclic group which is linked via a carbon atom;

(30) R$^3$ is a 5-6 membered heteroaryl group which is linked via a carbon atom;

(31) R$^3$ is selected from carbon linked pyrrolidinyl, imidazolidinyl, pyrazolidinyl, piperidinyl, piperazinyl, morpholinyl, thiomorpholinyl, oxazolidinyl, thienyl, furanyl, pyrrolyl, imidazolyl, pyrazolyl, thiazolyl, isothiazolyl, isoxazolyl, oxazolyl, oxadiazolyl, thiadiazolyl, triazolyl, tetrazolyl, pyridinyl, pyrazinyl, pyridazinyl or pyrimidinyl;

(32) R$^4$ is a group —NR$^{17}$R$^{18}$, wherein R$^{17}$ and R$^{18}$ are linked to form a 5 or 6 membered heterocyclic ring which optionally comprises, in addition to the nitrogen atom to which R$^{17}$ and R$^{18}$ are attached, one or two further heteroatoms selected from O, N or S, and wherein any S atoms that are present may be optionally oxidised to form an SO or SO$_2$ group, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom is optionally substituted by (1-4C)alkyl, hydroxy(1-4C)alkyl, or (1-4C)alkanoyl;

(33) R$^4$ is a group —NR$^{17}$R$^{18}$, wherein R$^{17}$ and R$^{18}$ are linked to form a 6 membered heterocyclic ring which optionally comprises, in addition to the nitrogen atom to which R$^{17}$ and R$^{18}$ are attached, one or two further heteroatoms selected from O, N or S, and wherein the ring is optionally substituted on any available carbon atom by one or two substituent groups selected from oxo, halo, hydroxy, cyano, or (1-4C)alkyl, and any available nitrogen atom is optionally substituted by (1-4C)alkyl, hydroxy(1-4C)alkyl or (1-4C)alkanoyl;

(34) R$^4$ is a group of formula:

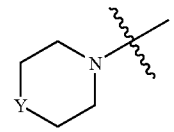

wherein Y is selected from O, S, NR$^y$, or CR$^z$, where R$^y$ is selected from hydrogen, (1-2C)alkyl, hydroxy(1-2C)alkyl, (1-2C)alkoxy(1-2C)alkyl, or (1-2C)alkanoyl, and R$^z$ is selected from hydrogen, hydroxy, (1-2C)alkyl, hydroxy(1-2C)alkyl, (1-2C)alkoxy(1-2C)alkyl, or (1-2C)alkanoyl;

(35) R$^4$ is a group of formula:

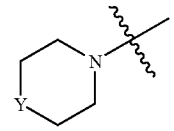

wherein Y is selected from O, NR$^y$, or CR$^z$, where R$^y$ is selected from hydrogen or (1-2C)alkyl, and R$^z$ is selected from hydrogen or hydroxy;

(36) R$^4$ is selected from morpholin-4-yl, 4-methylpiperazin-1-yl, or 4-hydroxypiperidin-1-yl;

(37) R$^4$ is morpholin-4-yl;

(38) A$^1$ or A is nitrogen and A$^3$ is CH;

(39) A$^2$ or A$^3$ is CH;

(40) A$^1$ is nitrogen and A$^2$ and A$^3$ are CH;

(41) A$^1$ and A$^3$ are both nitrogen and A$^2$ is CH;

(42) A$^2$ and A$^3$ are both nitrogen and A$^1$ is CH;

(43) Ring B is selected from —$CR^{22}$=$CR^{22}CR^{22}$=$CR^{22}$—, —N=$CR^{22}$—$CR^{22}$=$CR^{22}$—, —$CR^{22}$=N—$CR^{22}$=$CR^{22}$—, —$CR^{22}$=$CR^{22}$—N=$CR^{22}$—, —$CR^{22}$=$CR^{22}$—$CR^{22}$=N—, —N=$CR^{22}$—N=$CR^{22}$—, —$CR^{22}$=N—$CR^{22}$=N—, —N=$CR^{22}$—$CR^{22}$=N—, —N=N—$CR^{22}$=$CR^{22}$—, —$CR^{22}$=$CR^{22}$—N=N—, —$CR^{22}$=$CR^{22}$—O—, —O—$CR^{22}$=$CR^{22}$—, —$CR^{22}$=$CR^{22}$—S—, —S—$CR^{22}$=$CR^{22}$—, —$CR^{22}H$—$CR^{22}H$—O—, —O—$CR^{22}H$—$CR^{22}$—, —$CR^{22}H$—$CR^{22}H$—S—, —S—$CR^{22}H$—$CR^{22}H$—, —O—$CR^{22}H$—O—, —O—$CR^2$—O—, —O—$CR^{22}H$—$CR^{22}H$—O—, —S—$CR^{22}H$—S—, —S—$CR^{22}H$—$CR^{22}H$—S—, —$CR^{22}$=$CR^{22}$—$NR^{20}$—, —$NR^{20}$—$CR^{22}$=$CR^{22}$—, —$CR^{22}H$—$CR^{22}H$—$NR^{20}$—, —$NR^{20}$—$CR^{22}H$—$CR^{22}H$—, —N=$CR^{22}$—$NR^{20}$—, —$NR^{20}$—$CR^{22}$=N—, —$NR^{20}$—$CR^{22}H$—$NR^{20}$—, —$OCR^{22}$=N—, —N=$CR^{22}$—O—, —S—$CR^{22}$=N—, —N=$CR^{22}$—S—, —O—$CR^{22}H$—$NR^{20}$—, —$NR^{20}$—$CR^{22}H$—O—, —S—$CR^{22}H$—$NR^{20}$—, —$NR^{20}$—$CR^{22}H$—S—, —O—N=$CR^{22}$—, —$CR^{22}$=N—O—, —S—N=$CR^{22}$—, —$CR^{22}$=N—S—, —O—$NR^{20}$—$CR^{22}H$—, —$CR^{22}H$—$NR^{20}$—O—, —S—$NR^{20}$—$CR^{22}H$—, —$CR^{22}H$—$NR^{20}$—S—, —$NR^{20}$—N=$CR^{22}$—, —$CR^{22}$=N—$NR^{20}$—, —$NR^{20}$—$NR^{20}$—$CR^{22}H$—, —$CR^{22}H$—$NR^{20}$—$NR^{20}$—, —N=N—$NR^{20}$— or —$NR^{20}$—N=N—, where each $R^{20}$ is independently selected from hydrogen, $C_{1-6}$alkyl or $C_{1-6}$alkylcarbonyl, and where each $R^{22}$ is independently selected from hydrogen, halgeno or $C_{1-6}$alkyl;

(44) Ring B is selected from —O—$CR^{22}H$—O—, —$NR^{20}$—N=$CR^{22}$—, or —$CR^{22}$=N—$NR^{20}$—, where each $R^{20}$ is independently selected from hydrogen, $C_{1-6}$alkyl or $C_{1-6}$alkylcarbonyl, and where each $R^{22}$ is independently selected from hydrogen, halgeno or $C_{1-6}$alkyl;

(45) Ring B is selected from —$NR^{20}$—N=$CR^{22}$— or —$CR^{22}$=N—$NR^{20}$—, where each $R^{20}$ is independently selected from hydrogen, $C_{1-4}$alkyl or $C_{1-4}$alkylcarbonyl, and where each $R^{22}$ is independently selected from hydrogen, halgeno or $C_{1-4}$alkyl.

Suitably, n is 0 or 1.

Particular examples of B groups are set out below, and include for example groups B' as defined below. In particular B is —$OCH_2O$—, —$NR^{20}$—N=$CR^{22}$—, or —$CR^{22}$=N—$NR^{20}$—.

When n is other than zero, particular examples of $R^2$ or $R^{2a}$ groups are groups selected from halogeno, trifluoromethyl, cyano, hydroxy, $C_{1-6}$alkyl, $C_{2-8}$alkenyl, $C_{2-8}$alkynyl and $C_{1-6}$alkoxy.

For instance, $R^2$ or $R^{2a}$ may be selected from chloro, fluoro, bromo, trifluoromethyl, cyano, hydroxy, methyl, ethyl, ethynyl, methoxy and ethoxy.

In one embodiment, $R^2$ or $R^{2a}$ is halogeno, such as bromo, chloro or fluoro, and in particular chloro.

In a particular embodiment, n is 1 and $R^2$ or $R^{2a}$ is halogeno such as chloro.

Examples of ring B include those made up of a group of formula: —$CR^{22}$=$CR^{22}$—$CR^{22}$=$CR^{22}$—, —N=$CR^{22}$—$CR^{22}$=$CR^{22}$—, —$CR^{22}$=N—$CR^{22}$=$CR^{22}$—, —$CR^{22}$=$CR^{22}$—N=$CR^{22}$—, —$CR^{22}$=$CR^{22}$—$CR^{22}$=N—, —N=$CR^{22}$—N=$CR^{22}$—, —$CR^{22}$=N—$CR^{22}$=N—, —N=$CR^{22}$—$CR^{22}$=N—, —N=N—$CR^{22}$=$CR^{22}$—, —$CR^{22}$=$CR^{22}$—N=N—, —$CR^{22}$=$CR^{22}$—O—, —O—$CR^{22}$=$CR^{22}$—, —$CR^{22}$=$CR^{22}$—S—, —S—$CR^{22}$=$CR^{22}$—, —$CR^{22}H$—$CR^{22}H$—O—, —O—$CR^{22}H$—$CR^{22}H$—, —$CR^{22}H$—$CR^{22}H$—S—, —S—$CR^{22}H$—$CR^{22}H$—, —O—$CR^{22}H$—O—, —O—$CF_2$—O—, —O—$CR^{22}H$—$CR^{22}H$—O—, —S—$CR^{22}H$—S—, —S—$CR^{22}H$—$CR^{22}H$—S—, —$CR^{22}$=$CR^{22}$—$NR^{20}$—, —$NR^{20}$—$CR^{22}$=$CR^{22}$—, —$CR^{22}H$—$CR^{22}H$—$NR^{20}$—, —$NR^{20}$—$CR^{22}H$—$CR^{22}H$—, —N=$CR^{22}$—$NR^{20}$—, —$NR^{20}$—$CR^{22}$=N—, —$NR^{20}$—$CR^{22}H$—$NR^{20}$—, —$OCR^{22}$=N—, —N=$CR^{22}$—O—, —S—$CR^{22}$=N—, —N=$CR^{22}$—S—, —O—$CR^{22}H$—$NR^{20}$—, —$NR^{20}$—$CR^{22}H$—O—, —S—$CR^{22}H$—$NR^{20}$—, —$NR^{20}$—$CR^{22}H$—S—, —O—N=$CR^{22}$—, —$CR^{22}$=N—O—, —S—N=$CR^{22}$—, —$CR^{22}$=N—S—, —O—$NR^{20}$—$CR^{22}H$—, —$CR^{22}H$—$NR^{20}$—O—, —S—$NR^{20}$—$CR^{22}H$—, —$CR^{22}H$—$NR^{20}$—S—, —$NR^{20}$—N=$CR^{22}$—, —$CR^{22}$=N—$NR^{20}$—, —$NR^{20}$—$NR^{20}$—$CR^{22}H$—, —$CR^{22}H$—$NR^{20}$—$NR^{20}$—, —N=N—$NR^{20}$— or —$NR^{20}$—N=N—, where each $R^{20}$ is independently selected from hydrogen, $C_{1-6}$alkyl or $C_{1-6}$alkylcarbonyl, and where each $R^{22}$ is independently selected from hydrogen, halgeno or $C_{1-6}$alkyl.

In a particular embodiment, where a group B includes more than one group $R^{20}$ or $R^{22}$, at least one such group is hydrogen.

Examples of groups $R^{20}$ include hydrogen, methyl, ethyl or methylcarbonyl, in particular hydrogen.

Examples of groups $R^{22}$ include hydrogen, chloro, fluoro, methyl or ethyl, in particular hydrogen.

In a particular embodiment, ring B is a fused five-membered ring. Thus particular examples of B are groups of formula —CH=CH—O—, —O—CH=CH—, —CH=CH—S—, —S—CH=CH—, —$CH_2$—$CH_2$—O—, —O—$CH_2$—$CH_2$—, —$CH_2$—$CH_2$—S—, —S—$CH_2$—$CH_2$—, —O—$CH_2$—O—, —O—$CH_2$—$CH_2$—O—, —S—$CH_2$—S—, —S—$CH_2$—$CH_2$—S—, —CH=CH—$NR^{20}$—, —$NR^{20}$—CH=CH—, —$CH_2$—$CH_2$—$NR^{20}$—, —$NR^{20}$—$CH_2$—$CH_2$—, —N=CH—$NR^{20}$—, —$NR^{20}$—CH=N—, —$NR^{20}$—$CH_2$—$NR^{20}$—, —OCH=N—, —N=CH—O—, —S—CH=N—, —N=CH—S—, —O—$CH_2$—$NR^{20}$—, —$NR^{20}$—$CH_2$—O—, —S—$CH_2$—$NR^{20}$—, —$NR^{20}$—$CH_2$—S—, —O—N=CH—, —CH=N—O—, —S—N=CH—, —CH=N—S—, —O—$NR^{20}$—$CH_2$—, —$CH_2$—$NR^{20}$—O—, —S—$NR^{20}$—$CH_2$—, —$CH_2$—$NR^{20}$—S—, —$NR^{20}$—N=CH—, —CH=N—$NR^{20}$—, —$NR^{20}$—$NR^{20}$—$CH_2$—, —$CH_2$—$NR^{20}$—$NR^{20}$—, —N=N—$NR^{20}$— or —$NR^{20}$—N=N—.

Particular examples of $R^{20}$ include hydrogen, methyl, and acetyl. For instance, $R^{20}$ is hydrogen.

In one embodiment, Ring B includes one nitrogen atom. For instance, it is a group of formula —CH=CH—$NR^{20}$— or —$NR^{20}$—CH=CH—.

Ring B may also include two nitrogen atoms. For instance, it may be a group of formula —$NR^{20}$—N=CH—, —CH=N—$NR^{20}$—, —$NR^{20}$—$NR^{20}$—$CH_2$—, or —$CH_2$—$NR^{20}$—$NR^{20}$— and in particular is a group —$NR^{20}$—N=CH— or —CH=N—$NR^{20}$—. Such rings, in particular where $R^{20}$ is hydrogen form a particular aspect of the invention.

In another embodiment, Ring B includes one nitrogen and one oxygen atom. It is therefore suitably selected from —O—N=CH—, —CH=N—O—, —O—$NR^{20}$—$CH_2$— or —$CH_2$—$NR^{20}$—O—.

In yet a further embodiment, Ring B is a group of formula —O—$CH_2$—O— or —O—$CF_2$—O—, in particular —O—$CH_2$—O—.

Where n is 1 or more, a substituent $R^3$ is suitably positioned on the available ortho-carbon atom of the ring, forming a compound of formula (IA)

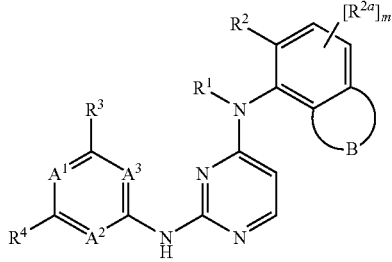

(IA)

where $A^1$, $A^2$, $A^3$, B, $R^1$, $R^2$, $R^3$ and $R^4$ have any one of the definitions set out above in relation to formula (I), $R^{2a}$ is a group $R^2$ as defined above, and in particular is halogeno, and m is 0, 1 or 2.

Suitably in formula (IA), m is 0.

In particular, examples of compounds of formula (I) are compounds of formula (IB)

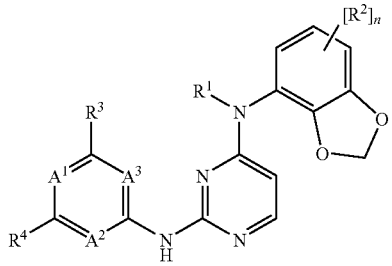

(IB)

wherein $A^1$, $A^2$, $A^3$, $R^1$, $R^2$, $R^3$, $R^4$ and n have any one of the definitions set out above in relation to formula (I).

In another embodiment, the invention provides a compound of formula (IC)

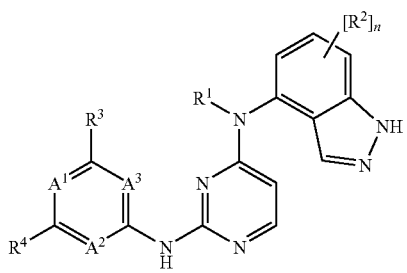

(IC)

where $A^1$, $A^2$ $A^3$, $R^1$, $R^2$, $R^3$, $R^4$ and n have any one of the definitions set out above in relation to formula (I).

Particular options for $A^1$, $A^2$ $A^3$, $R^1$, $R^2$, $R^3$, $R^4$, n and $R^{20}$ in formula (IC) are as set out above in relation to formula (I). Suitably in the case of the compounds of formula (IC), n is 0.

In another embodiment, the invention provides a compound of formula (ID)

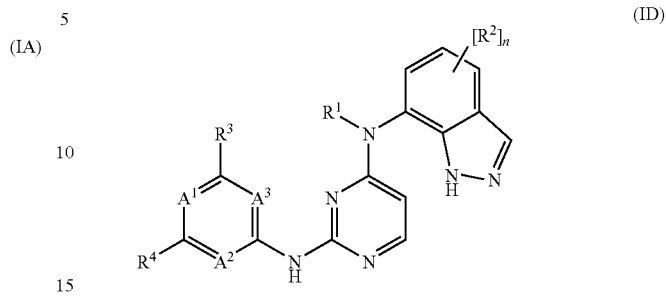

(ID)

where $A^1$, $A^2$ $A^3$, $R^1$, $R^2$, $R^3$, $R^4$ and n have any one of the definitions set out above in relation to formula (I).

Particular options for $A^1$, $A^2$ $A^3$, $R^1$, $R^2$, $R^3$, $R^4$ n and $R^{20}$ in formula (ID) are as set out above in relation to formula (I). Suitably in the case of the compounds of formula (ID), n is 0.

In another embodiment, the invention provides a compound of formula (IE), or a pharmaceutically acceptable salt thereof

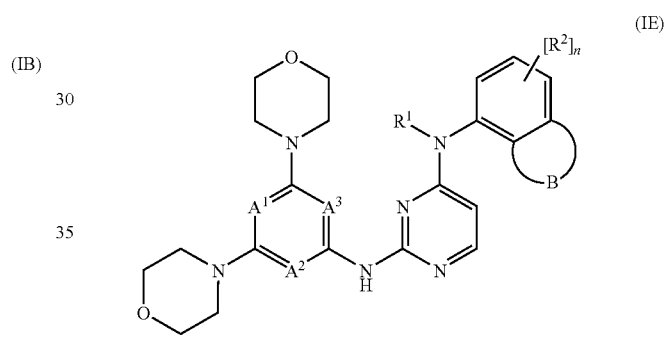

(IE)

where:
$A^1$ is N and $A^2$ and $A^3$ are both CH;
$A^1$ and $A^2$ are both N and $A^3$ is CH; or
$A^2$ is N and $A^1$ and $A^3$ are both CH;
B is —OCH$_2$O—, —NH—N═CH—, or —CH═N—NH—;
$R^1$ is hydrogen or a (1-4C)alkyl group;
$R^2$ is halogeno; and
n is 0 or 1.

In one particular embodiment, the invention provides a compound of formula (IE) as defined above where $A^1$ is N and $A^2$ and $A^3$ are both CH.

In another embodiment, the invention provides a compound of formula (IE) as defined above where B is —OCH$_2$O— or —CH═N—NH—.

In a further embodiment, the invention provides a compound of formula (IE) as defined above where $R^1$ is a (1-4C) alkyl group, and in one particular embodiment $R^1$ is methyl.

In a further embodiment, the invention provides a compound of formula (IE) as defined above where $R^2$ is chloro, and in one particular embodiment n is 1 and $R^2$ is chloro positioned on the available carbon atom in the ortho position relative to the amine linkage.

In a further embodiment, the invention provides a compound of formula (IE) as defined above where n is 0.

In a further group of compounds of formula (I), (IA), (IB), (IC), (ID) or (IE), at least one of $A^2$ or $A^3$ is —CH—.

In yet a further group of compounds of formula (I), (IA), (IB), (IC), (ID) or (IE), at least one of $A^1$ or $A^2$ is N and $A^3$ is CH or at least one of $A^1$ or $A^3$ is N and $A^2$ is CH.

In yet a further group of compounds of formula (I), (IA), (IB), (IC), (ID) or (IE), $A^1$ is N and $A^2$ and $A^3$ are CH.

Particular examples of compounds of formula (I) are:
N4-(5-chlorobenzo[d][1,3]dioxol-4-yl)-N2-(2,6-dimorpholinopyridin-4-yl)pyrimidine-2,4-diamine;
N4-(5-chlorobenzo[d][1,3]dioxol-4-yl)-N2-(2,6-dimorpholinopyridin-4-yl)-N4-methylpyrimidine-2,4-diamine;
N2-(2,6-dimorpholinopyridin-4-yl)-N4-(1H-indazol-4-yl)pyrimidine-2,4-diamine;
N'-(1H-indazol-4-yl)-N'-methyl-N-(2-morpholin-4-ylpyridin-4-yl)pyrimidine-2,4-diamine;
N-(2,6-dimorpholin-4-ylpyridin-4-yl)-N'-(1H-indazol-4-yl)-N'-methyl-pyrimidine-2,4-diamine;
N-(4-chloro-6-morpholin-4-yl-pyridin-2-yl)-N'-(1H-indazol-4-yl)-N'-methyl-pyrimidine-2,4-diamine;
N-(2,6-dimorpholin-4-ylpyrimidin-4-yl)-N'-(1H-indazol-4-yl)-N'-methyl-pyrimidine-2,4-diamine;
N-(2-chloro-6-morpholin-4-yl-pyridin-4-yl)-N'-(1H-indazol-4-yl)-N'-methyl-pyrimidine-2,4-diamine;
N'-(5-chloro-1,3-benzodioxol-4-yl)-N-(4-morpholino-2-pyridyl)pyrimidine-2,4-diamine;
N'-(5-chloro-1,3-benzodioxol-4-yl)-N-(6-morpholino-2-pyridyl)pyrimidine-2,4-diamine;
N-(4,6-dimorpholin-4-ylpyrimidin-2-yl)-N'-(1H-indazol-4-yl)-N'-methyl-pyrimidine-2,4-diamine; or
N'-(5-chloro-1,3-benzodioxol-4-yl)-N-[2-methyl-6-(4-methylpiperazin-1-yl)pyrimidin-4-yl]pyrimidine-2,4-diamine, or a pharmaceutically acceptable salt thereof.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds of the formula (I) may have chiral centres and some may have geometric isomeric centres (E- and Z-isomers), and it is to be understood that the invention encompasses all such optical, diastereoisomers and geometric isomers that possess EphB4 or EphA2 inhibitory activity.

The invention relates to any and all tautomeric forms of the compounds of the formula (I) that possess EphB4 or EphA2 inhibitory activity.

It is also to be understood that certain compounds of the formula (I) can exist in solvated as well as unsolvated forms such as, for example, hydrated forms. It is to be understood that the invention encompasses all such solvated forms which possess EphB4 or EphA2 inhibitory activity. This activity may be evaluated using laboratory techniques referred to hereinafter.

The synthesis of optically active forms may be carried out by standard techniques of organic chemistry well known in the art, for example by synthesis from optically active starting materials or by resolution of a racemic form.

Compounds of formula I can be prepared by various conventional methods as would be apparent to a chemist. In particular, compounds of formula I may be prepared by reacting a compound of formula (II):

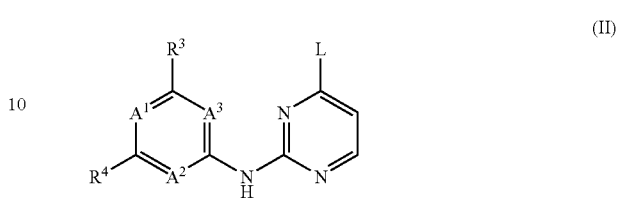

where $A^1$, $A^2$, $A^3$, $R^3$ and $R^4$ is as defined in relation to formula I with the proviso that any functional groups are optionally protected, and L is a leaving group, with a compound of formula (III)

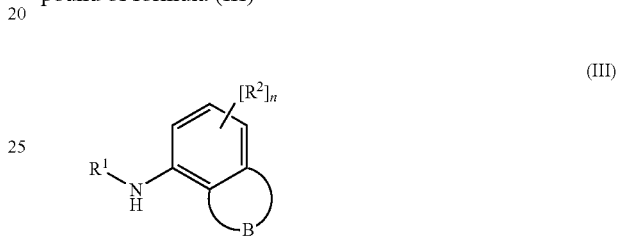

where B, $R^1$, n and $R^2$ are as defined in relation to formula I provided that any functional groups are optionally protected. Thereafter, any protecting groups can be removed using conventional methods, and if required, the compound of formula I can be converted to a different compound of formula I or a salt, again using conventional chemical methods well known in the art.

Suitable leaving groups L are halogeno such as chloro. The reaction is suitably carried out in an organic solvent such as a $C_{1-6}$alkanol, for instance, n-butanol, isopropanol or 2-pentanol, dimethylacetamide (DMA), or N-methylpyrrolidine (NMP) or mixtures thereof. An acid, and in particular an inorganic acid such as hydrochloric acid, is suitably added to the reaction mixture. The reaction is suitably conducted at elevated temperatures for example at from 80-150° C., conveniently at the reflux temperature of the solvent.

Alternatively, the reaction between (II) and (III) may be catalysed by transition metals complexes, such as palladium catalysts. Examples of suitable palladium catalysts include $Pd_2(dba)_3$ (tris(dibenzylideneacetone)dipalladium), $Pd(PPh_3)_4$ and $Pd(OAc)_2$. This palladium catalysed reaction conveniently carried out in the presence of a suitable base, such as potassium carbonate, cesium carbonate, potassium phosphate, sodium tert-butoxide, or 1,8-diazabicyclo[5.4.0]undec-7-ene (DBU). Suitable solvents for such a reaction include toluene, dioxane or ethylene glycol dimethylether (DME). Suitable ligands for use in such a reaction include Xantphos (4,5-bis(diphenylphosphino)-9,9-dimethylxanthene), BINAP (2,2'-bis(diphenylphosphino)-1,1'-binaphtyl) or DPPF (1,1'-bis(diphenylphosphino)ferrocene). The reaction is conveniently carried out at an elevated temperature, generally at the reflux temperature of the particular solvent used. A temperature of 90-140° C. would be typical.

Compounds of formula (II) may be prepared by various methods including for example, where L is a halogen, by reacting a compound of formula (IV)

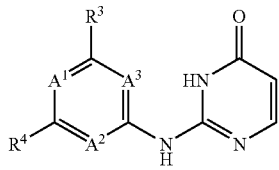
(IV)

where $A^1$, $A^2$, $A^3$, $R^3$ and $R^4$ are as defined in relation to formula I, with a suitable halogenating agent such as phosphorus oxychloride.

The reaction is conducted under reactions conditions appropriate to the halogenating agent employed. For instance, it may be conducted at elevated temperatures, for example of from 50-100° C., in an organic solvent such as acetonitrile or dichloromethane (DCM).

Compounds of formula (IV) are suitably prepared by reacting a compound of formula (V)

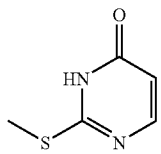

with a compound of formula (VI)

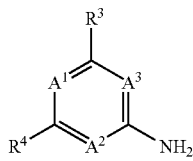
(VI)

where $A^1$, $A^2$, $A^3$, $R^3$ and $R^4$ are as defined in relation to formula I.

The reaction is suitably effected in an organic solvent such as diglyme, again at elevated temperatures, for example from 120-180° C., and conveniently at the reflux temperature of the solvent.

Compounds of formula (II), in which L is chloro, may also be prepared by reacting a compound of formula XIII XIII
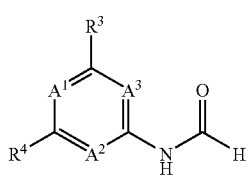

wherein $A^1$, $A^2$, $A^3$, $R^3$ and $R^4$ are as defined in relation to Formula I, with 4-chloro-2-methylsulfonylpyrimidine in the presence of a suitable base, such as sodium hydride.

Alternatively, compounds of formula I may be prepared by reacting a compound of formula (VII)

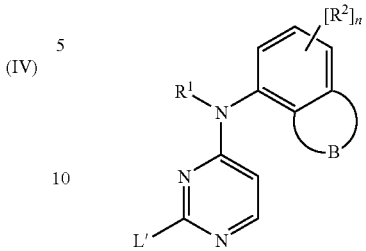
(VII)

where B, $R^1$, n, and $R^2$ are as defined in relation to formula I provided that any functional groups can be optionally protected, and L' is a leaving group such as those described above in relation to formula (II) or may be —SO$_2$Me, with a compound of formula (VI) as defined above.

Again, any protecting groups can be removed using conventional methods, and if required, the compound of formula I can be converted to a different compound of formula I or a salt, again using conventional chemical methods.

Conditions for carrying out such a reaction are broadly similar to those required for the reaction between compounds (II) and (III) described above.

Compounds of formula (VII) are suitably prepared by reacting a compound of formula (III) as defined above, where any amine groups in particular are optionally protected, with a compound of formula (VIII)

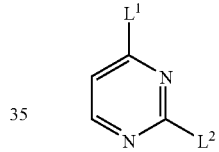
(VIII)

where $L^1$ and $L^2$ are leaving groups such as halogen, and in particular chloro.

The reaction is suitably effected in the presence of a base for example, an organic base such as triethylamine or N,N-diisopropylethylamine. The reaction is also suitably carried out at an elevated temperature, for example between 80 and 120° C. in a suitable organic solvent such as a $C_{1-6}$alkanol, for instance, ethanol. The reaction can also be performed in presence of a strong base such as sodium hydride, in an organic solvent such as DMA. When the basic reaction conditions are used, depressed temperatures, for example from −20° C. to 20° C., conveniently at about 0° C. are suitably employed.

Compounds of formula (VII) where $R^1$ is other than hydrogen can also be prepared by reacting a compound of formula (IX)

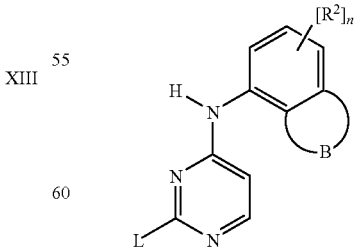
(IX)

wherein L is a leaving group as defined hereinbefore and B and $R^2$ and n are as defined in relation to Formula I with a compound $R^{1'}$—X where X is a suitable leaving group such as halogen and $R^{1'}$ is as defined above in relation to Formula I but is other than hydrogen.

This reaction is conveniently performed using a base such as caesium carbonate in a suitable solvent, such as, for example, dimethylformamide.

Compounds of formula I where $R^1$ is other than hydrogen may also be prepared from compounds of formula (I) where $R^1$ is hydrogen by the reaction of a compound formula (X)

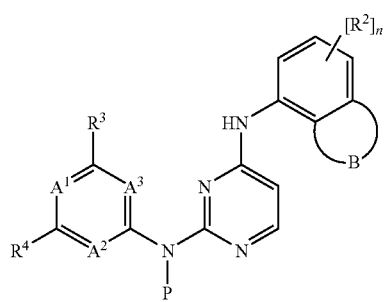

wherein $A^1$, $A^2$, $A^3$, B, $R^2$, n, $R^3$ and $R^4$ are as defined above in relation to Formula I; with a compound

where X is a suitable leaving group such as halogen and $R^1$ is as defined above in relation to Formula I but is other than hydrogen, and P is a suitable protecting group for this reaction, for example a 4-methoxybenzyl group.

This reaction is conveniently performed using a strong base such as sodium hydride in a suitable solvent, for example dimethylformamide. Such a reaction forms an example of a reaction in which a compound of formula (I) is converted to a different compound of formula (I), but there may be many other examples of suitable conversion reactions as would be apparent to a chemist.

Another method for preparing compounds of formula I is to react a compound of formula (XI)

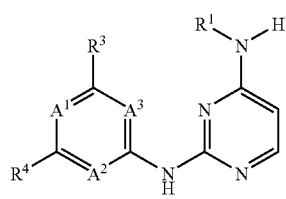

wherein $A^1$, $A^2$, $A^3$, $R^1$, $R^3$ and $R^4$ are as defined above in relation to Formula I; with a compound of formula (XII)

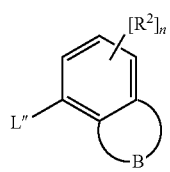

wherein B, $R^2$ and n are as defined above in relation to Formula I and L" is halogen, for example bromo, where any functional groups are protected as necessary.

This reaction is suitably carried out in the presence of a suitable catalyst such as a palladium catalyst. Examples of suitable palladium catalysts include $Pd_2(dba)_3$ (tris(dibenzylideneacetone)dipalladium), $Pd(PPh_3)_4$ and $Pd(OAc)_2$. This palladium catalysed reaction conveniently carried out in the presence of a suitable base, such as potassium carbonate, cesium carbonate, potassium phosphate, sodium tert-butoxide, or 1,8-diazabicyclo[5.4.0]undec-7-ene (DBU). Suitable solvents for such a reaction include toluene, dioxane or ethylene glycol dimethylether (DME). Suitable ligands for use in such a reaction include Xantphos (4,5-bis(diphenylphosphino)-9,9-dimethylxanthene), BINAP (2,2'-bis(diphenylphosphino)-1,1'-binaphtyl) or DPPF (1,1'-bis(diphenylphosphino) ferrocene). The reaction is conveniently carried out at an elevated temperature, generally at the reflux temperature of the particular solvent used. A temperature of 90-140° C. would be typical.

Compounds of formula (III) are either known compounds or they can be prepared from known compounds using analogous methods, which would be apparent to the skilled chemist. For example, compounds of formula (III) where $R^1$ is hydrogen may be obtained by hydrogenation of compounds of formula (XIII)

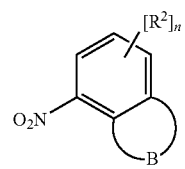

where B, $R^2$ and n are as defined in relation to formula (I), and where any functional groups are protected as necessary. Suitable hydrogenation conditions include the use of a hydrogen gas under pressure in the presence of a platinum catalyst. The reaction is suitably effected in an organic solvent such as ethanol and ethyl acetate. Other examples of compounds of formula (III) and their preparation are described in WO2001094341.

Compounds of formula (VIII) are also either known compounds or they can be prepared from known compounds using analogous methods, which would be apparent to the skilled chemist.

Compounds of formula (VI) are also either known compounds or they can be prepared from known compounds using routine methods.

Compounds of the formula I can be converted into further compounds of the formula I using standard procedures conventional in the art. Examples of the types of conversion reactions that may be used to convert a compound of formula I to a different compound of formula I include introduction of a substituent by means of an aromatic substitution reaction or of a nucleophilic substitution reaction, reduction of substituents, alkylation of substituents and oxidation of substituents. The reagents and reaction conditions for such procedures are well known in the chemical art.

Particular examples of aromatic substitution reactions include the introduction of an alkyl group using an alkyl halide and Lewis acid (such as aluminium trichloride) under Friedel Crafts conditions; and the introduction of a halogeno group. Particular examples of nucleophilic substitution reactions include the introduction of an alkoxy group or of a monoalkylamino group, a dialkyamino group or a N-containing heterocycle using standard conditions. Particular examples of reduction reactions include the reduction of a carbonyl group to a hydroxy group with sodium borohydride or of a nitro group to an amino group by catalytic hydrogenation with a nickel catalyst or by treatment with iron in the presence of hydrochloric acid with heating.

The preparation of particular compounds of formula I, such as compounds of formula IA, IB, IC, ID or IE using the above-described methods form a further aspect of the invention.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Compounds of the formula I can be converted into further compounds of the formula I using standard procedures conventional in the art.

Examples of the types of conversion reactions that may be used to convert a compound of formula (I) to a different compound of formula (I) include introduction of a substituent by means of an aromatic substitution reaction or of a nucleophilic substitution reaction, reduction of substituents, alkylation of substituents and oxidation of substituents. The reagents and reaction conditions for such procedures are well known in the chemical art.

Particular examples of aromatic substitution reactions include the introduction of an alkyl group using an alkyl halide and Lewis acid (such as aluminium trichloride) under Friedel Crafts conditions; and the introduction of a halogeno group. Particular examples of nucleophilic substitution reactions include the introduction of an alkoxy group or of a monoalkylamino group, a dialkyamino group or a N-containing heterocycle using standard conditions. Particular examples of reduction reactions include the reduction of a carbonyl group to a hydroxy group with sodium borohydride or of a nitro group to an amino group by catalytic hydrogenation with a nickel catalyst or by treatment with iron in the presence of hydrochloric acid with heating.

The preparation of particular compounds of formula (I), such as compounds of formula (IA), (IC) and (IE) using the above-described methods form a further aspect of the invention.

According to a further aspect of the invention there is provided a pharmaceutical composition, which comprises a compound of the formula (I) and in particular a compound of formula (IA), (IB), (IC) or (IE), or a pharmaceutically acceptable salt or pro-drug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg/m$^2$ body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

As a result of their activity in screens described below, the compounds of the present invention are expected to be useful in the treatment of diseases or medical conditions mediated alone or in part by EphB4 or EphA2, i.e. the compounds may be used to produce an EphB4 or EphA2 inhibitory effect in a warm-blooded animal in need of such treatment. Thus, the compounds of the present invention provide a method for treating the proliferation of malignant cells characterised by inhibition of EphB4 or EphA2, i.e. the compounds may be used to produce an anti-proliferative effect mediated alone or in part by the inhibition of EphB4 or EphA2.

According to another aspect of the present invention there is provided a compound of the formula (I), (IA), (IB), (IC), (ID) or (IE), or a pharmaceutically acceptable salt or pro-drug thereof, as defined hereinbefore for use in a method of treatment of the human or animal body by therapy.

Thus according to a further aspect of the invention there is provided a compound of the formula (I), (IA), (IB), (IC), (ID) or (IE), or a pharmaceutically acceptable salt or pro-drug thereof, as defined hereinbefore for use as a medicament.

According to a further aspect of the invention there is provided the use of a compound of the formula (I), (IA), (IB), (IC), (ID) or (IE), or a pharmaceutically acceptable salt or pro-drug thereof, as defined hereinbefore in the manufacture of a medicament for use in the production of an EphB4 or EphA2 inhibitory effect, in a warm-blooded animal such as man.

According to a further feature of this aspect of the invention there is provided a method for producing an EphB4 or EphA2 inhibitory effect in a warm-blooded animal, such as man, in need of such treatment which comprises administering to said animal an effective amount of a compound of the formula (I), or a pharmaceutically acceptable salt or pro-drug thereof, as defined hereinbefore.

According to a further aspect of the invention there is provided the use of a compound of the formula (I), (IA), (IB), (IC), (ID) or (IE), or a pharmaceutically acceptable salt or pro-drug thereof, as defined hereinbefore in the manufacture of a medicament for use in the production of an anti-angiogenic effect in a warm-blooded animal such as man.

According to a further feature of this aspect of the invention there is provided a method for producing an anti-angiogenic effect in a warm-blooded animal, such as man, in need of such treatment which comprises administering to said animal an effective amount of a compound of the formula (I), (IA), (IB), (IC), (ID) or (IE), or a pharmaceutically acceptable salt or pro-drug thereof, as defined hereinbefore.

According to an additional feature of this aspect of the invention there is provided a method of treating cancer in a warm-blooded animal, such as man, in need of such treatment which comprises administering to said animal an effective amount of a compound of the formula (I), (IA), (IB), (IC), (ID) or (IE), or a pharmaceutically acceptable salt or pro-drug thereof, as defined hereinbefore.

According to a further feature of the invention there is provided a compound of the formula (I), (IA), (IB), (IC), (ID) or (IE), or a pharmaceutically acceptable salt or pro-drug thereof, as defined hereinbefore in the manufacture of a medicament for use in the treatment of cancer.

According to an additional feature of this aspect of the invention there is provided a compound of the formula (I), (IA), (IB), (IC), (ID) or (IE), or a pharmaceutically acceptable salt or pro-drug thereof, as defined hereinbefore, for use in the treatment of cancer.

According to an additional feature of this aspect of the invention there is provided a compound of the formula (I), (IA), (IB), (IC), (ID) or (IE), or a pharmaceutically acceptable salt or pro-drug thereof, as defined hereinbefore, for use in the treatment of solid tumour disease, in particular neuroblastomas, breast, liver, lung and colon cancer or leukemias.

According to an additional feature of this aspect of the invention there is provided the use of a compound of the formula (I), (IA), (IB), (IC), (ID) or (IE), or a pharmaceutically acceptable salt or pro-drug thereof, as defined hereinbefore, for use in the manufacture of a medicament for the treatment of cancer.

In a further aspect of the present invention there is provided the use of a compound of the formula (I), (IA), (IB), (IC), (ID) or (IE), or a pharmaceutically acceptable salt or pro-drug thereof, as defined hereinbefore, in the manufacture of a medicament for use in the treatment of solid tumour disease, in particular neuroblastomas, breast, liver, lung and colon cancer or leukemias.

In a further aspect of the present invention there is provided a method of treating neuroblastomas, breast, liver, lung and colon cancer or leukemias in a warm-blooded animal, such as man, in need of such treatment which comprises administering to said animal an effective amount of a compound of the formula (I), or a pharmaceutically acceptable salt or pro-drug thereof, as defined hereinbefore.

The EphB4 or EphA2 inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the anti-angiogenic treatment defined hereinbefore may be: surgery, radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib,), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO 01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) Cell cycle inhibitors including for example CDK inhibitors (eg flavopiridol) and other inhibitors of cell cycle checkpoints (eg checkpoint kinase); inhibitors of aurora kinase and other kinases involved in mitosis and cytokinesis regulation (eg mitotic kinesins); and other histone deacetylase inhibitors; and (xi) differentiation agents (for example retinoic acid and vitamin D).

According to this aspect of the invention there is provided a pharmaceutical composition comprising a compound of the formula (I) as defined hereinbefore and an additional antitumour substance as defined hereinbefore for the conjoint treatment of cancer.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

In addition to their use in therapeutic medicine, the compounds of formula (I), (IA), (IB), (IC), (ID) or (IE), and their pharmaceutically acceptable salts thereof, are also useful as pharmacological tools in the development and standardisation of in vitro and in vivo test systems for the evaluation of the effects of inhibitors of anti-angiogenic activity in laboratory animals such as cats, dogs, rabbits, monkeys, rats and mice, as part of the search for new therapeutic agents.

The invention will now be illustrated in the following Examples in which, generally:

(i) operations were carried out at ambient temperature, i.e. in the range 17 to 25° C. and under an atmosphere of an inert gas such as nitrogen or argon unless otherwise stated;

(ii) in general, the course of reactions was followed by thin layer chromatography (TLC) and/or analytical high pressure liquid chromatography (HPLC); the reaction times that are given are not necessarily the minimum attainable;

(iii) when necessary, organic solutions were dried over anhydrous magnesium sulphate, work-up procedures were carried out using traditional layer separating techniques or an ALLEXIS (MTM) automated liquid handler, evaporations were carried out either by rotary evaporation in vacuo or in a Genevac HT-4/EZ-2.

(iv) yields, where present, are not necessarily the maximum attainable, and when necessary, reactions were repeated if a larger amount of the reaction product was required;

(v) in general, the structures of the end-products of the Formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; proton NMR chemical shift values were measured on the delta scale using either a Bruker Spectrospin DPX300 spectrometer operating at a field strength of 300 MHz, a Bruker Dpx400 operating at 400 MHz or a Bruker Advance operating at 500 MHz. The following abbreviations have been used: s, singlet; d, doublet; t, triplet; q, quartet; m, multiplet; br, broad;

(vi) unless stated otherwise compounds containing an asymmetric carbon and/or sulphur atom were not resolved;

(vii) intermediates were not necessarily fully purified but their structures and purity were assessed by TLC, analytical HPLC, infra-red (IR) and/or NMR analysis;

(viii) unless otherwise stated, column chromatography (by the flash procedure) and medium pressure liquid chromatography (MPLC) were performed on Merck Kieselgel silica (Art. 9385);

(ix) preparative HPLC was performed on C18 reversed-phase silica, for example on a Waters 'Xterra' preparative reversed-phase column (5 microns silica, 19 mm diameter, 100 mm length) using decreasingly polar mixtures as eluent, for example decreasingly polar mixtures of water (containing 1% acetic acid or 1% aqueous ammonium hydroxide (d=0.88)) and acetonitrile;

(x) the following analytical HPLC methods were used; in general, reversed-phase silica was used with a flow rate of about 1 ml per minute and detection was by Electrospray Mass. Spectrometry and by UV absorbance at a wavelength of 254 nm; for each method Solvent A was water and Solvent B was acetonitrile; the following columns and solvent mixtures were used:—

Preparative HPLC was performed on C18 reversed-phase silica, on a Phenomenex "Gemini" preparative reversed-phase column (5 microns silica, 110A, 21.1 mm diameter, 100 mm length) using decreasingly polar mixtures as eluent, for example decreasingly polar mixtures of water (containing 0.1% formic acid or 0.1% ammonia) as solvent A and acetonitrile as solvent B; either of the following preparative HPLC methods were used:

Method A: a solvent gradient over 9.5 minutes, at 25 mls per minute, from a 85:15 mixture of solvents A and B respectively to a 5:95 mixture of solvents A and B.

Method B: a solvent gradient over 9.5 minutes, at 25 mls per minute, from a 60:40 mixture of solvents A and B respectively to a 5:95 mixture of solvents A and B.

(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) the following abbreviations have been used:—
DMSO dimethylsulphoxide
NMP 1-methyl-2-pyrrolidinone
DMA N,N-dimethylacetamide
DCM Dichloromethane

EXAMPLE 1

N4-(5-chlorobenzo[d][1,3]dioxol-4-yl)-N2-(2,6-dimorpholinopyridin-4-yl)pyrimidine-2,4-diamine

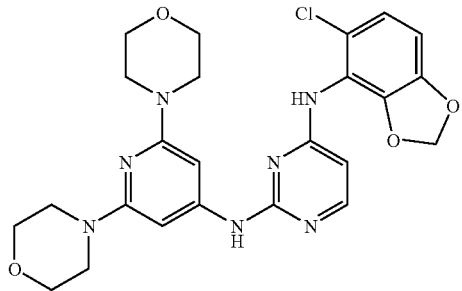

2,6-Dimorpholinopyridin-4-amine (140 mg, 0.53 mmol), 2-chloro-N-(5-chlorobenzo[d][1,3]dioxol-4-yl)pyrimidin-4-amine (150 mg, 0.53 mmol), 1,8-diazabicyclo-[5.4.0]-undec-7-ene (0.158 mL, 1.06 mmol), bis(dibenzylideneacetone)palladium(0) (45.5 mg, 0.08 mmol) and 9,9-dimethyl-4,5-bis (diphenylphosphino)xanthene (92 mg, 0.16 mmol) were dissolved in dioxane (3 mL) and sealed into a microwave tube. The reaction was degassed, purged with nitrogen and heated at 120° C. overnight. The reaction mixture was filtered off and washed thoroughly with dichloromethane. The filtrate was concentrated to dryness, diluted with dichloromethane (15 ml), washed with water (30 ml) and brine (15 ml), dried over magnesium sulfate and concentrated. The crude product was purified by flash chromatography on silica gel eluting with 0 to 50% ethyl acetate in dichloromethane. The solvent was evaporated to dryness to afford N4-(5-chlorobenzo[d][1,3]dioxol-4-yl)-N2-(2,6-dimorpholinopyridin-4-yl)pyrimidine-2,4-diamine (80 mg, 29.6%) as a pale beige foam. NMR Spectrum: (DMSOd$_6$) 3.09-3.25 (m, 8H), 3.57-3.70 (m, 8H), 6.00 (s, 2H), 6.17 (d, 1H), 6.52 (s, 2H), 6.91 (d, 1H), 7.04 (d, 1H), 8.02 (d, 1H), 9.02 (s, 1H), 9.03 (s, 1H); Mass spectrum: MH$^+$ 512.

The 2-chloro-N-(5-chlorobenzo[d][1,3]dioxol-4-yl)pyrimidin-4-amine used as starting material was made as follows:

Sodium hydride (13.4 g, 60% dispersion in mineral oil) was added portionwise to (5-chloro-1,3-benzodioxol-4-yl) amine (11.5 g, prepared as described in WO2001094341) in DMA (100 ml) at 0° C. 2,4-Dichloropyrimidine (10 g) was added and the reaction warmed to room temperature and stirred overnight. The reaction was quenched cautiously with water, the solution filtered and concentrated and the residue dissolved in DCM, washed with water and brine, dried and concentrated to give 2-chloro-N-(5-chlorobenzo[d][1,3]dioxol-4-yl)pyrimidin-4-amine as a dark brown oil that was used without further purification (16 g, 85%); NMR Spectrum (300 MHz, DMSO) 6.10 (s, 2H), 6.58 (d, 1H), 6.94 (d, 1H), 7.05 (d, 1H), 8.15 (d, 1H), 9.76 (s, 1H); Mass Spectrum M$^+$ 284.

The 2,6-dimorpholinopyridin-4-amine used as starting material was made as follows:

A mixture of 4-amino-2,6-dichloro-pyridine (900 mg, 5.52 mmol), morpholine (4.8 ml, 55.2 mmol) and DMA (1.0 ml, 11 mmol) was heated in a Personal Chemistry EMRYS™ Optimizer EXP microwave synthesisor at 240° C. for 30 minutes. After cooling, morpholine was removed in vacuo, the residue was treated with 30% aqueous ammonium hydroxide and the resulting mixture was extracted with methylene chloride. Evaporation of the solvent and purification of the residue on silica gel (3% MeOH in DCM) followed by trituration in ether provided 2,6-dimorpholin-4-ylpyridin-4-amine (950 mg, 65% yield). NMR Spectrum (500 MHz, CDCl$_3$) 3.39-3.42 (m, 8H), 3.77-3.79 (m, 8H), 3.91 (bs, 2H), 5.39 (s, 2H). Mass Spectrum: MH$^+$ 265.

EXAMPLE 2

N4-(5-chlorobenzo[d][1,3]dioxol-4-yl)-N2-(2,6-dimorpholinopyridin-4-yl)-N4-methylpyrimidine-2,4-diamine

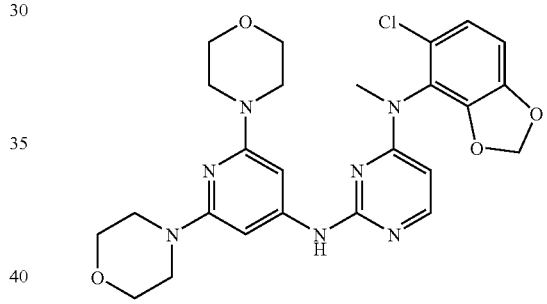

2,6-Dimorpholinopyridin-4-amine (160 mg, 0.60 mmol) and 2-chloro-N-(5-chlorobenzo[d][1,3]dioxol-4-yl)-N-methylpyrimidin-4-amine (180 mg, 0.60 mmol) were reacted according to the procedure in Example 1 to give N4-(5-chlorobenzo[d][1,3]dioxol-4-yl)-N2-(2,6-dimorpholinopyridin-4-yl)-N4-methylpyrimidine-2,4-diamine (80 mg, 25.2%) as a pale yellow foam. NMR Spectrum (CDCl$_3$) 3.23-3.58 (m, 11H), 3.72-3.90 (m, 8H), 5.65 (s, 1H), 6.03 (s, 2H), 6.50 (s, 2H), 6.79 (d, 1H), 6.99 (d, 1H), 7.17 (s, 1H), 7.90 (s, 1H); Mass spectrum: MH$^+$ 526.

2-Chloro-N-(5-chlorobenzo[d][1,3]dioxol-4-yl)-N-methylpyrimidin-4-amine used as starting material was made as follows:

2-Chloro-N-(5-chloro[d][1,3]benzodioxol-4-yl)pyrimidin-4-amine (1.5 g, 5.30 mmol, see Example 1, Starting material) was dissolved in DMF (30 mL). Potassium carbonate (1.1 g, 8.0 mmol) was added, followed by iodomethane (0.36 mL, 5.8 mmol) and the mixture was stirred at room temperature overnight. After evaporation under reduced pressure, the residue was dissolved in ethyl acetate, washed with water and brine, dried and evaporated to yield a brown oil (1.54 g, 98%) which solidified on standing; NMR Spectrum (500 MHz, DMSO-d$_6$ at 353° K) 3.33 (s, 3H), 6.29 (s, 2H), 7.12 (bs, 1H), 7.00 (d, 1H), 7.10 (d, 1H), 8.12 (bs, 1H); Mass Spectrum MH$^+$ 298.

EXAMPLE 3

N2-(2,6-dimorpholinopyridin-4-yl)-N4-(1H-indazol-4-yl)pyrimidine-2,4-diamine

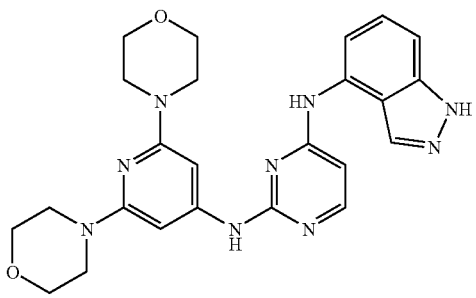

N-(2-chloropyrimidin-4-yl)-1-(4-methoxybenzyl)-1H-indazol-4-amine (400 mg, 1.09 mmol) and 2,6-dimorpholinopyridin-4-amine (289 mg, 1.09 mmol) were reacted according to procedure of Example 1. After filtration of the solids and evaporation of the solvents, the resulting gum was dissolved in TFA (8.2 mL) and anisole (0.594 mL, 5.47 mmol) and sealed into a microwave tube. The reaction was heated to 130° C. over a period of 30 minutes in a Personal Chemistry EMRYS™ Optimizer EXP microwave synthesisor. The reaction mixture was concentrated to dryness, diluted with dichloromethane (20 ml), washed with water (20 ml), brine (20 ml), dried over magnesium sulfate and concentrated. The crude product was purified by flash chromatography on silica gel eluting with 0 to 5% methanol in dichloromethane. The solvent was evaporated to dryness. The resulting solid was triturated with diethyl ether/petroleum ether (1/1), collected by filtration and dried under vacuum to give N2-(2,6-dimorpholinopyridin-4-yl)-N4-(1H-indazol-4-yl)pyrimidine-2,4-diamine (178 mg, 34.4%) as a pale beige solid. NMR Spectrum: (DMSOd$_6$) 3.17 (bs, 8H), 3.61 (bs, 8H), 6.47 (s, 1H), 6.59 (s, 2H), 7.22 (s, 1H), 7.27 (s, 1H), 7.79 (s, 1H), 8.12 (s, 1H), 8.21 (s, 1H), 9.16 (s, 1H), 9.46 (s, 1H), 13.06 (s, 1H); Mass spectrum: MH$^+$ 474.

N-(2-chloropyrimidin-4-yl)-1-(4-methoxybenzyl)-1H-indazol-4-amine used as starting material was made as follows:

To a suspension of 4-nitro-1H-indazole (10 g, 61.30 mmol) and potassium carbonate (9.32 g, 67.43 mmol) in DMF (100 mL) at 25° C. was added 4-methoxybenzyl chloride (9.14 mL, 67.43 mmol). The resulting mixture was stirred at 110° C. for 2 hours. The reaction mixture was cooled and diluted with water. The aqueous layer was extracted with DCM (2×100 mL). The organic layer was dried over MgSO$_4$, filtered and concentrated. The residue was purified by flash chromatography on silica gel eluting with 0 to 2% ethyl acetate in dichloromethane. The solvent was evaporated to dryness to afford 1-(4-methoxybenzyl)-4-nitro-1H-indazole (9.00 g, 51.8%) as a orange solid. NMR Spectrum: (DMSOd$_6$) 3.70 (s, 3H), 5.73 (s, 2H), 6.87 (d, 2H), 7.25 (d, 2H), 7.65 (dd, 1H), 8.17 (d, 1H), 8.34 (d, 1H), 8.54 (s, 1H).

A suspension of 1-(4-methoxybenzyl)-4-nitro-1H-indazole (9 g, 31.77 mmol) and platinum(IV) oxide (0.433 g, 1.91 mmol) in ethanol (150 mL)/ethyl acetate (10 mL) was hydrogenated under 40 psi at 25° C. for 2 hours. The resulting mixture was filtered and the filtrate was concentrated to dryness to afford 1-(4-methoxybenzyl)-1H-indazol-4-amine (8.03 g, 100%) as a yellow-orange solid. Mass spectrum: MH$^+$ 254.

A suspension of 2,4-dichloropyrimidine (3.71 g, 24.87 mmol), 1-(4-methoxybenzyl)-1H-indazol-4-amine (6 g, 23.69 mmol) and N,N-diisopropylethylamine (4.54 mL, 26.06 mmol) in ethanol (60 mL) was stirred at 90° C. for 65 hours. The reaction mixture was concentrated to dryness, diluted with ethyl acetate (100 ml), washed with water (100 ml) and brine (100 ml), dried over magnesium sulfate and concentrated. The crude product was purified by flash chromatography on silica gel eluting with 5 to 70% ethyl acetate in petroleum ether. The solvent was evaporated to dryness to afford N-(2-chloropyrimidin-4-yl)-1-(4-methoxybenzyl)-1H-indazol-4-amine (5.53 g, 64%) as a pink solid. NMR Spectrum: (DMSOd$_6$) 3.70 (s, 3H), 5.57 (s, 2H), 6.86 (d, 2H), 6.93 (d, 1H), 7.22 (d, 2H), 7.37 (dd, 1H), 7.48 (d, 1H), 7.59 (d, 1H), 8.22 (d, 1H), 8.23 (s, 1H), 10.13 (s, 1H); Mass spectrum: MH$^+$ 366

EXAMPLES 4 TO 8

N-(2-Chloropyrimidin-4-yl)-1-(4-methoxybenzyl)-N-methyl-1H-indazol-4-amine (304 mg, 0.80 mmol) the corresponding aminoheteroaryl (0.80 mmol), 1,8-diazabicyclo-[5.4.0]-undec-7-ene (0.239 mL, 1.60 mmol), bis(dibenzylideneacetone)palladium(0) (69 mg, 0.12 mmol) and 9,9-dimethyl-4,5-bis(diphenylphosphino)xanthene (139 mg, 0.24 mmol) were suspended in dioxane (5 mL) and sealed into a microwave tube. The reaction mixture was degassed, purged with nitrogen and heated at 120° C. overnight in an oil bath. The reaction mixture was allowed to cool to room temperature, filtered off and washed with dichloromethane. The filtrate was concentrated to dryness. The residue was dissolved in a solution of 20% water in trifluoroacetic acid (5 mL) and the reaction was heated to 75° C. for 24 hours. The mixture was concentrated to dryness, taken up in methanol (2.5 mL)-toluene (2.5 mL) and concentrated to dryness. The residue was dissolved in DMF (1 mL), neutralized with 7N methanolic ammonia, and purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford the desired product.

N-(2-Chloropyrimidin-4-yl)-1-(4-methoxybenzyl)-N-methyl-1H-indazol-4-amine used as starting material was made as follows:

Methyl iodide (1.021 mL, 16.40 mmol) was added dropwise to a stirred suspension of N-(2-chloropyrimidin-4-yl)-1-(4-methoxybenzyl)-1H-indazol-4-amine (4 g, 10.93 mmol, Example 3 starting material) and potassium carbonate (2.267 g, 16.40 mmol) in DMF (40 mL) at 0° C. under nitrogen. The resulting suspension was stirred at 0° C. for 15 minutes and was allowed to warm to room temperature. The reaction mixture was stirred at room temperature overnight, filtered off and washed with ethyl acetate. The filtrate was concentrated to dryness, diluted with dichloromethane (40 ml), washed with water (40 ml), brine (40 ml), dried over magnesium sulfate and concentrated. The residue was purified by flash chromatography on silica gel eluting with 0 to 45% ethyl acetate in petroleum ether to afford N-(2-chloropyrimidin-4-yl)-1-(4-methoxybenzyl)-N-methyl-1H-indazol-4-amine (3.4 g, 82%) as a pale orange solid. NMR Spectrum: (DMSOd$_6$) 3.50 (s, 3H), 3.71 (s, 3H), 5.63 (s, 2H), 6.19 (d, 1H), 6.89 (d, 2H), 7.16 (d, 1H), 7.29 (d, 2H), 7.49 (dd, 1H), 7.81 (d, 1H), 7.96 (d, 1H), 8.00 (s, 1H); Mass spectrum: MH$^+$ 380.

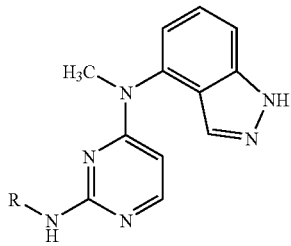

| Example No. | Name | R (Starting aniline) | Molecular ion (MH+) | NMR Spectrum |
|---|---|---|---|---|
| 4[a] | N'-(1H-indazol-4-yl)-N'-methyl-N-(2-morpholin-4-ylpyridin-4-yl)pyrimidine-2,4-diamine | | 403 | 3.29-3.34(m, 4H), 3.57(s, 3H), 3.65-3.70(m, 4H), 5.80 (d, 1H), 7.04(d, 1H), 7.11(d, 1H), 7.33(s, 1H), 7.44(dd, 1H), 7.56(d, 1H), 7.86(d, 1H), 7.91(d, 1H), 7.94(s, 1H), 9.43(s, 1H), 13.33(bs, 1H) |
| 5[b] | N-(2,6-dimorpholin-4-ylpyridin-4-yl)-N'-(1H-indazol-4-yl)-N'-methyl-pyrimidine-2,4-diamine | | 488 | 3.25-3.31(m, 8H), 3.56(s, 3H), 3.63-3.70(m, 8H), 5.73 (d, 1H), 6.70(s, 2H), 7.10(d, 1H), 7.43 (dd, 1H), 7.54(d, 1H), 7.87(d, 1H), 7.93(s, 1H), 8.18(s, 1H), 13.32(bs, 1H) |
| 6[c] | N-(4-chloro-6-morpholin-4-ylpyridin-2-yl)-N'-(1H-indazol-4-yl)-N'-methyl-pyrimidine-2,4-diamine | | 437 | 3.34-3.50(m, 4H), 3.55(s, 3H), 3.63-3.71(m, 4H), 5.84 (d, 1H), 6.42(s, 1H), 7.11(d, 1H), 7.44 (dd, 1H), 7.56(d, 1H), 7.61(bs, 1H), 7.92(s, 1H), 7.93(d, 1H), 8.95(s, 1H), 13.32(bs, 1H) |
| 7[d] | N-(2,6-dimorpholin-4-ylpyrimidin-4-yl)-N'-(1H-indazol-4-yl)-N'-methyl-pyrimidine-2,4-diamine | | 489 | 3.31-3.41(m, 8H), 3.56(s, 3H), 3.58-3.65(m, 8H), 5.83 (d, 1H), 7.05(d, 1H), 7.11(s, 1H), 7.43 (dd, 1H), 7.56(d, 1H), 7.92(d, 1H), 7.93(s, 1H), 8.67(s, 1H), 13.35(b,s 1H) |

-continued

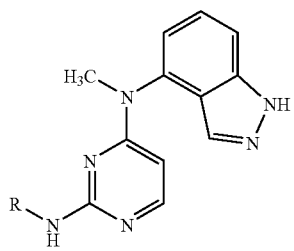

| Example No. | Name | R (Starting aniline) | Molecular ion (MH+) | NMR Spectrum |
|---|---|---|---|---|
| 8[e] | N-(2-chloro-6-morpholin-4-yl-pyridin-4-yl)-N'-(1H-indazol-4-yl)-N'-methyl-pyrimidine-2,4-diamine | (structure: 2-chloro-6-morpholinopyridin-4-yl) | 437 | 3.28-3.35(m, 4H), 3.57(s, 3H), 3.63-3.71(m, 4H), 5.83 (d, 1H), 7.11(d, 1H), 7.18(s, 1H), 7.21(s, 1H), 7.44(dd, 1H), 7.57(d, 1H), 7.93(d, 1H), 7.94(d, 1H), 9.67(s, 1H), 13.33 (bs, 1H) |

[a]2-Morpholinopyridin-4-amine used as starting material was made as follows:
A suspension of 2-chloro-6-morpholinopyridine-4-amine (567 mg, 2.65 mmol, see note e) and 10% palladium on charcoal (57 mg) in ethyl acetate (8 mL) - ethanol (1.6 mL) was hydrogenated under 1 atm at at room temperature for 5 hours. N,N-Diisopropylethylamine (0.55 mL) was added. The mixture was filtered and the filtrate was concentrated to dryness. The residue was diluted with ethyl acetate, washed with saturated aqueous sodium bicarbonate and brine, dried over magnesium sulfate and concentrated to afford 2-morpholinopyridin-4-amine (265 mg, 56%) as a white solid. NMR Spectrum: (DMSOd$_6$) 3.37-3.43(m, 4H), 3.69-3.76(m, 4H), 6.03(d, 1H), 6.32(dd, 1H), 7.53(bs, 2H), 7.62(d, 1H); Mass spectrum: MH+ 180

[b]the compound was repurified by flash chromatography on silica gel eluting with 0 to 4% methanol in dichloromethane.

[c]the compound was repurified by flash chromatography on silica gel eluting with 0 to 4% methanol in dichloromethane.

4-Chloro-6-morpholin-4-yl-pyridin-2-amine used as starting material was made as follows:

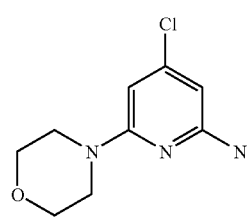

A mixture of 2-amino-4,6-dichloro-pyridine (900 mg, 5.52 mmol, described in Rec. Trav. Chim. Pays-Bas 1950, vol. 69, p. 673-690), morpholine (4.80 ml, 55.2 mmol) and DMSO (0.39 ml, 5.52 mmol) was heated in a Personal Chemistry EMRYS ™ Optimizer EXP microwave synthesiser at 170° C. for 30 minutes. After cooling, morpholine was removed in vacuo, the residue was treated with 30% ammonium hydroxide and the resulting mixture was extracted with methylene chloride. Evaporation of the solvent and purification of the residue on silica gel (3 to 4% MeOH in DCM) provided 4-chloro-6-morpholin-4-yl-pyridin-2-amine (890 mg, 72% yield) and its isomer 6-chloro-4-morpholin-4-yl-pyridin-2-amine (190 mg, 16% yield). NMR Spectrum (500 MHz, CDCl3) 3.43-3.45(m, 4H), 3.76-3.78(m, 4H), 4.30(bs, 2H), 5.91(s, 1H), 5.97(s, 1H). Mass Spectrum: MH+ 214.

-continued

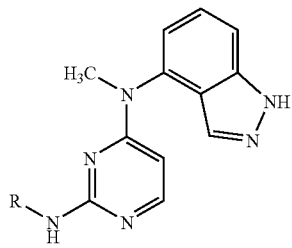

| Example No. | Name | R (Starting aniline) | Molecular ion (MH+) | NMR Spectrum |
|---|---|---|---|---|

$^d$In the deprotection step with 20% water in TFA, the mixture was stirred at 75° C. for 24 hours, and then at 140° C. for 15 minutes.

2,6-Dimorpholin-4-ylpyrimidin-4-amine used as starting material was made as follows:

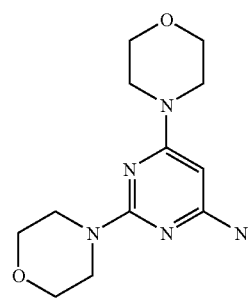

A mixture of 4-amino-2,6-dichloropyrimidine (1.64 g, 10.0 mmol), morpholine (8.7 ml, 100 mmol) and DMA (1.90 ml, 20 mmol) was heated at 180° C. for 1 hour. After cooling, morpholine was removed in vacuo and the residue was purified on silica gel (2 to 4% MeOH in DCM) to provide 2,6-dimorpholin-4-ylpyrimidin-4-amine (2.1 g, 79% yield) as a white solid. NMR Spectrum (500 MHz, CDCl3) 3.45-3.49(m, 4H), 3.71-3.75(m, 12H), 4.37(bs, 2H), 5.07(s, 1H). Mass Spectrum: MH+ 266.

$^e$2-chloro-6-morpholin-4-yl-pyridin-4-amine used as starting material was made as follows:

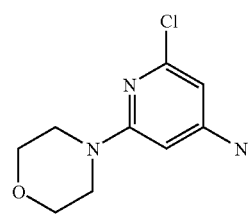

A mixture of 4-amino-2,6-dichloro-pyridine (2.0 g, 12.2 mmol), morpholine (10.7 ml, 123 mmol) and DMSO (0.87 ml, 12.3 mmol) was heated in a Personal Chemistry EMRYS ™ Optimizer EXP microwave synthesisor at 170° C. for 1 hour. After cooling, morpholine was removed in vacuo, the residue was treated with 30% ammonium hydroxide and the resulting mixture was extracted with methylene chloride. Evaporation of the solvent and purification of the residue on silica gel (2 to 3% MeOH in DCM) provided 2-chloro-6-morpholin-4-yl-pyridin-4-amine (1.4 g, 53% yield). NMR Spectrum (500 MHz, CDCl3) 3.42-3.44(m, 4H), 3.76-3.78(m, 4H), 4.07(bs, 2H), 5.69(s, 1H), 6.04(s, 1H). Mass Spectrum: MH+ 214.

Examples 9, 10 and 11 were prepared following the same procedure as Example 1 except that the heating was performed at 150° C. for 10 minutes in a microwave reactor. The crude mixture was purified on a preparative HPLC-MS system (Column: C18, 5 microns, 19 mm diameter, 100 mm length, elution with a gradient of water and acetonitrile containing 2 g/l of ammonium carbonate). Evaporation of the collected fractions gave the desired compounds.

EXAMPLE 9

N'-(5-chloro-1,3-benzodioxol-4-yl)-N-(4-morpholino-2-2pyridyl)pyrimidine-2,4-diamine

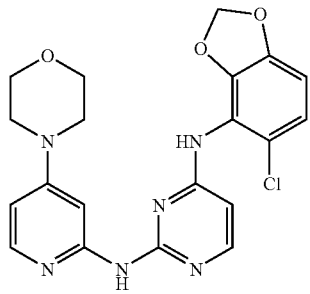

Prepared from 4-morpholinopyridin-2-amine (described in Bioorg. Med. Chem. Lett. 2006, vol. 16, p. 839) in 31% yield.

NMR Spectrum (500 MHz, DMSO-$d_6$) 3.01 (m, 4H), 3.66 (m, 4H), 5.99 (s, 2H), 6.16 (d, 1H), 6.46 (dd, 1H), 6.91 (d, 1H), 7.05 (d, 1H), 7.56 (s, 1H), 7.88 (d, 1H), 8.05 (d, 1H), 8.70 (br s, 1H), 9.09 (br s, 1H). Mass Spectrum MH+ 427

EXAMPLE 10

N'-(5-chloro-1,3-benzodioxol-4-yl)-N-(6-morpholino-2-pyridyl)pyrimidine-2,4-diamine

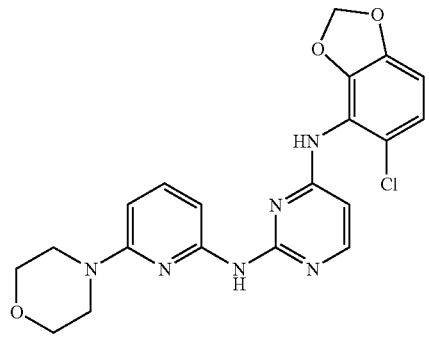

Prepared from 6-morpholinopyridin-2-amine (described in WO2002014311, p. 111) in 26% yield.

NMR Spectrum (500 MHz, DMSO-$d_6$) 3.38 (m, 4H), 3.66 (m, 4H), 6.03 (s, 2H), 6.19 (d, 1H), 6.31 (d, 1H), 6.93 (d, 1H), 7.04 (d, 1H), 7.25 (t, 1H), 7.33 (d, 1H), 8.03 (d, 1H), 8.47 (s, 1H), 9.11 (s, 1H). Mass Spectrum MH+ 427

EXAMPLE 11

N-(4,6-dimorpholin-4-ylpyrimidin-2-yl)-N'-(1H-indazol-4-yl)-N'-methyl-pyrimidine-2,4-diamine

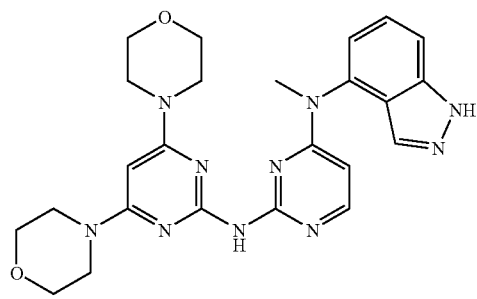

This compound was prepared from 4,6-dimorpholinopyrimidin-2-amine following the same procedure as Example 4, using potassium carbonate (20 eq.) instead of 1,8-diazabicyclo-[5.4.0]-undec-7-ene and toluene as the solvent.

NMR Spectrum (500 MHz, DMSO-$d_6$) 3.51-3.57 (m, 8H), 3.52 (s, 3H), 3.61-3.67 (m, 8H), 5.61 (s, 1H), 5.69 (d, 1H), 7.09 (d, 1H), 7.43 (dd, 1H), 7.54 (d, 1H), 7.82 (d, 1H), 7.89 (s, 1H), 8.54 (s, 1H), 13.32 (s, 1H) Mass Spectrum MH+ 489

4,6-dimorpholinopyrimidin-2-amine was prepared using the following procedure: 2-amino-4,6-dichloropyrimidine (1 g, 6.10 mmol) and morpholine (5.33 ml, 60.9 mmol) were dissolved in DMA (1.1 ml) and sealed into a microwave tube. The mixture was heated to 150° C. over a period of 20 minutes in the microwave reactor. The reaction mixture was diluted with AcOEt, filtered and the filtrate concentrated to give an oil. The crude product was purified by flash chromatography on silica gel eluting with 0 to 4% methanol in dichloromethane. The solvent was evaporated to dryness to afford 4,6-dimorpholinopyrimidin-2-amine (1.15 g, 71%) as a white foam.

NMR Spectrum (500 MHz, DMSO-d6) 3.38-3.44 (m, 8H), 3.57-3.64 (m, 8H), 5.31 (s, 1H), 5.65 (bs, 2H)

EXAMPLE 12

N'-(5-chloro-1,3-benzodioxol-4-yl)-N-[2-methyl-6-(4-methylpiperazin-1-yl)pyrimidin-4-yl]pyrimidine-2,4-diamine

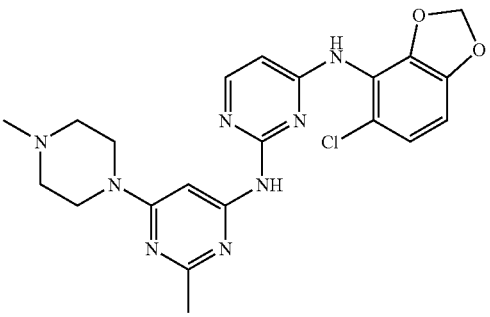

2-Methyl-6-(4-methylpiperazin-1-yl)pyrimidin-4-amine (71 mg), palladium acetate (1 mg), Xantphos (24 mg), caesium carbonate (166 mg) and 2-chloro-N-(5-chloro-1,3-benzodioxol-4-yl)pyrimidin-4-amine (117 mg) were dissolved in dioxane (4 ml) under nitrogen and heated in a microwave reactor at 150° C. for 60 minutes. The reaction was cooled and partitioned between ethyl acetate and water. The organic layer was dried and concentrated to give a brown solid that was purified by reverse phase chromatography to give N'-(5-chloro-1,3-benzodioxol-4-yl)-N-[2-methyl-6-(4-methylpiperazin-1-yl)pyrimidin-4-yl]pyrimidine-2,4-diamine as a yellow solid (25 mg, 13%); NMR Spectrum (300 MHz, CDCl$_3$) 2.30 (s, 3H), 2.37 (s, 3H), 2.55 (br s, 4H), 3.64 (br s, 4H), 5.90 (s, 2H), 5.95 (d, 1H), 6.58-6.68 (m, 1H), 6.78-6.95 (m, 1H), 7.40 (s, 1H), 8.09 (d, 1H); Mass Spectrum M$^+$ 455.

The 2-methyl-6-(4-methylpiperazin-1-yl)pyrimidin-4-amine used as starting material was prepared as follows:

6-Amino-2-methylpyrimidin-4-ol (5 g) was suspended in phosphorous oxychloride (50 ml) and heated at 80° C. for 1 hour. A few drops of DMF was added and the reaction heated to 105° C. for 3 hours to give an orange solution. The reaction was cooled, concentrated in vacuo and azeotroped with toluene. The residue was cautiously partitioned between ethyl acetate and ice-cold saturated aqueous sodium bicarbonate solution. The organic layer was separated, washed with water and brine, dried and concentrated in vacuo to afford 6-chloro-2-methylpyrimidin-4-amine as a yellow solid which was used without further purification (3 g, 68%); NMR Spectrum (300 MHz, CDCl$_3$) 2.50 (s, 3H), 5.00 (br s, 2H), 6.30 (s, 1H); Mass Spectrum MH$^+$+CH$_3$CN 185. 6-Chloro-2-methylpyrimidin-4-amine (2.45 g) was suspended in 1-methylpiperazine (24 ml) and the reaction heated at 140° C. for 20 minutes in a microwave reactor. The reaction was cooled and concentrated in vacuo. The residue was dissolved in methanol and neutralised with polymer-bound carbonate resin for 1 hour, then filtered and concentrated to give an orange solid that was triturated with ethyl acetate to give 2-methyl-6-(4-methylpiperazin-1-yl)pyrimidin-4-amine as a cream solid (2.64 g, 81%); NMR Spectrum (300 MHz, CDCl$_3$) 2.20 (s, 3H), 2.30 (s, 3H), 2.40 (m, 4H), 3.50 (m, 4H), 4.40 (br s, 2H), 5.40 (s, 1H); Mass Spectrum MH$^+$ 208.

EXAMPLE 13

Biological Assays

A) In vitro EphB4 Enzyme Assay

This assay detects inhibitors of EphB4-mediated phosphorylation of a polypeptide substrate using Alphascreen™ luminescence detection technology. Briefly, recombinant EphB4 was incubated with a biotinylated-polypeptide substrate (biotin-poly-GAT) in presence of magnesium-ATP. The reaction was stopped by addition of EDTA, together with streptavidin-coated donor beads which bind the biotin-substrate containing any phosphorylated tyrosine residues. Anti-phosphotyrosine antibodies present on acceptor beads bind to phosphorylated substrate, thus bringing the donor & acceptor beads into close proximity. Subsequent excitation of the donor beads at 680 nm generated singlet oxygen species that interact with a chemiluminescer on the acceptor beads, leading to light emission at 520-620 nm. The signal intensity is directly proportional to the level of substrate phosphorylation and thus inhibition is measured by a decrease in signal.

Aqueous Compound Preparation:

Test compounds were prepared as 10 mM stock solutions in DMSO (Sigma-Aldrich Company Ltd, Gillingham, Dorset SP8 4XT Catalogue No. 154938) and serially diluted with 5% DMSO to give a range of test concentrations at 6× the required final concentration. A 2 µl aliquot of each compound dilution was transferred to appropriate wells of low volume white 384-well assay plates (Greiner, Stroudwater Business Park, Stonehouse, Gloucestershire, GL10 3SX, Cat No. 784075) in duplicate. Each plate also contained control wells: maximum signal was created using wells containing 2 µl of 5% DMSO, and minimum signal corresponding to 100% inhibition were created using wells containing 2 µl of 0.5M EDTA (Sigma-Aldrich Company Ltd, Catalogue No. E7889).

Acoustic Compound Preparation:

Test compounds were prepared in 100% DMSO and dispensed in multiples of 2.5 nl droplets into the target wells of the assay plate using a Labcyte Echo550 (Sunnyvale, Calif. 94089, USA). To ensure that each well contained a total of 120 nl DMSO the wells were all backfilled as required. Maximum control wells contained DMSO, minimum control wells contained 120 nl of a compound at a concentration sufficient to completely inhibit enzyme activity. The test range of compounds was 100× the required final concentration.

For the assay using aqueous prepared compounds, in addition to the compound or control, each well of the assay plate contained; 10 µl of assay mix containing final buffer (10 mM Tris, 100 µM EGTA, 10 mM magnesium acetate, 4 µM ATP, 500 µM DTT, 1 mg/ml BSA), 0.25 ng of recombinant active EphB4 (amino acids 563-987; Swiss-Prot Acc. No. P54760) (ProQinase GmbH, Breisacher Str. 117, D-79106 Freiburg, Germany, Catalogue No 0178-0000-3) and 5 nM of the poly-GAT substrate (CisBio International, BP 84175, 30204 Bagnols/Ceze Cedex, France, Catalogue No. 61GATBLB). Assay plates were then incubated at room temperature for 1 hour.

For assays using compounds prepared via acoustic dispensing, the assay mix was adjusted such that the final assay volume of 12 ul contained the same concentration of reagent as 10 ul of assay mix used when aqueous compounds were tested.

Regardless of the method of compound preparation, the reaction was stopped by addition of 5 µl/well stop buffer (10 mM Tris, 495 mM EDTA, 1 mg/ml BSA) containing 0.25 ng each of AlphaScreen anti-phosphoTyrosine-100 acceptor beads and streptavidin-coated donor beads (Perkin Elmer, Catalogue No 6760620M). The plates were sealed under natural lighting conditions, wrapped in aluminium foil and incubated in the dark for a further 20 hours.

The resulting assay signal was determined on the Perkin Elmer EnVision plate reader. The minimum value was subtracted from all values, and the signal plotted against compound concentration to generate IC$_{50}$ data. The method used to generate the compound dilutions was recorded with the IC$_{50}$ value in the database. Data from compounds prepared using acoustic dispensing were marked "Echo" and the remaining results were marked "Genesis". Compounds of the invention were tested in the in vitro EphB4 enzyme assay and the IC$_{50}$ values so obtained are presented in Table A below.

TABLE A

| Example Number | EphB4 enzyme assay Mean IC$_{50}$ value (µM) | Method of compound preparation |
|---|---|---|
| 1 | 0.501* | Genesis |
| 2 | 0.605* | Genesis |
| 3 | 0.243 | Genesis |
| 4 | 0.146* | Genesis |
|   | 0.003 | Echo |
| 5 | 0.553* | Genesis |
|   | 0.002 | Echo |
| 6 | 0.973* | Genesis |
|   | 0.007 | Echo |
| 7 | 0.778* | Genesis |
|   | 0.003 | Echo |
| 8 | 0.445* | Genesis |
|   | 0.004 | Echo |
| 9 | 0.170 | Genesis |
|   | 0.052* | Echo |
| 10 | 0.817* | Genesis |
|   | 0.064* | Echo |
| 11 | 3.03* | Genesis |
|   | 0.486* | Echo |
| 12 | 6.440 | Genesis |

*Tested once only.

B) In vitro EphB4 Cell Assay

The assay identifies inhibitors of cellular EphB4 by measuring a decrease in phosphorylation of EphB4 following treatment of cells with compound. The endpoint assay used a sandwich ELISA to detect EphB4 phosphorylation status. Briefly, Myc-tagged EphB4 from treated cell lysate was captured on the ELISA plate via an anti-c-Myc antibody. The phosphorylation status of captured EphB4 was then measured using a generic phosphotyrosine antibody conjugated to HRP via a colourimetric output catalysed by HRP, with level of EphB4 phosphorylation directly proportional to the colour intensity. Absorbance was measured spectrophotometrically at 450 nm.

Full length human EphB4 (Swiss-Prot Acc. No. P54760) was cloned using standard techniques from cDNA prepared from HUVEC using RT-PCR. The cDNA fragment was then sub-cloned into a pcDNA3.1 expression vector containing a Myc-His epitope tag to generate full-length EphB4 containing a Myc-His tag at the C-terminus (Invitrogen Ltd. Paisley, UK). CHO-K[1] cells (LGC Promochem, Teddington, Middlesex, UK, Catalogue No. CCL-61) were maintained in HAM's F12 medium (Sigma-Aldrich Company Ltd, Gillingham, Dorset SP8 4XT, Catalogue No. N4888) containing 10% heat-inactivated foetal calf serum (PAA lab GmbH, Pasching, Austria Catalogue No. PAA-A15-043) and 1% glutamax-1 (Invitrogen Ltd., Catalogue No. 35050-038) at 37° C. with 5% $CO_2$. CHO-K1 cells were engineered to stably express the EphB4-Myc-His construct using standard stable transfection techniques, to generate cells hereafter termed EphB4-CHO.

For each assay 10,000 EphB4-CHO cells were seeded into each well of Costar 96-well tissue-culture plate (Fisher Scientific UK, Loughborough, Leicestershire, UK., Catalogue No. 3598) and cultured overnight in full media. On day 2, the cells were incubated overnight in 90 μl/well of media containing 0.1% Hyclone stripped-serum (Fisher Scientific UK, Catalogue No. SH30068.02). Test compounds were prepared as 10 mM stock solutions in DMSO (Sigma-Aldrich Company Ltd, Gillingham, Dorset SP8 4XT Catalogue No. 154938) and serially diluted with serum-free media to give a range of test concentrations at 10× the required final concentration. A 10 μl aliquot of each compound dilution was transferred to the cell plates in duplicate wells, and the cells incubated for 1 hour at 37° C. Each plate also contained control wells: a maximum signal was created using untreated cells, and minimum signal corresponding to 100% inhibition was created using wells containing a reference compound known to abolish EphB4 activity.

Recombinant ephrin-B2-Fc (R&D Systems, Abingdon Science Park, Abingdon, Oxon OX14 3NB UK, Catalogue No. 496-EB), a Fc-tagged form of the cognate ligand for EphB4, was pre-clustered at a concentration of 3 μg/ml with 0.3 μg/ml anti-human IgG, Fc fragment specific (Jackson ImmunoResearch Labs, Northfield Business Park, Soham, Cambridgeshire, UK CB7 5UE, Catalogue No. 109-005-008) in serum-free media for 30 minutes at 4° C. with occasional mixing. Following compound treatment, cells were stimulated with clustered ephrin-B2 at a final concentration of 1 μg/ml for 20 minutes at 37° C. to induce EphB4 phosphorylation. Following stimulation, the medium was removed and the cells lysed in 100 μl/well of lysis buffer (25 mM Tris HCl, 3 mM EDTA, 3 mM EGTA, 50 mM NaF, 2 mM orthovanadate, 0.27M Sucrose, 10 mM β-glycerophosphate, 5 mM sodium pyrophosphate, 2% Triton X-100, pH 7.4).

Each well of an ELISA Maxisorp 96-well plate (Nunc; Fisher Scientific UK, Loughborough, Leicestershire, UK., Catalogue No. 456537) was coated overnight at 4° C. with 100 μl of anti-c-Myc antibody in Phosphate Buffered Saline (10 μg/ml; produced at AstraZeneca). Plates were washed twice with PBS containing 0.05% Tween-20 and blocked with 250 μl/well 3% TopBlock (Fluka) (Sigma-Aldrich Company Ltd, Gillingham, Dorset SP8 4XT, Catalogue No. 37766) for a minimum of 2 hours at room temperature. Plates were washed twice with PBS/0.05% Tween-20 and incubated with 100 μl/well cell lysate overnight at 4° C. ELISA plates were washed four times with PBS/0.05% Tween-20 and incubated for 1 hour at room temperature with 100 μl/well HRP-conjugated 4G10 anti-phosphotyrosine antibody (Upstate, Dundee Technology Park, Dundee, UK, DD2 1 SW, Catalogue No. 16-105) diluted 1:6000 in 3% Top Block. ELISA plates were washed four times with PBS/0.05% Tween-20 and developed with 100 μl/well TMB substrate (Sigma-Aldrich Company Ltd, Catalogue No. T0440). The reaction was stopped after 15 minutes with the addition of 25 μl/well 2M sulphuric acid. The absorbances were determined at 450 nm using the Tecan SpectraFluor Plus. The minimum value was subtracted from all values, and the signal plotted against compound concentration to generate $IC_{50}$ data.

Compounds of the invention were active in the above assays, for instance, generally showing $IC_{50}$ values of less than 30 μM, in Assay A and Assay B. For instance the Compound of Example 3 above showed an $IC_{50}$ of 0.243 μM in assay A and $IC_{50}$ of 0.026 μM in assay B. Preferred compounds of the invention had an $IC_{50}$ value of less than 10 μM in Assay A and less than 0.5 μM in Assay B.

C) In vitro EphA2 Enzyme Assay

This assay detects inhibitors of EphA2-mediated phosphorylation of a polypeptide substrate using Alphascreen™ luminescence detection technology. Briefly, recombinant EphA2 was incubated with a biotinylated-polypeptide substrate (biotin-poly-GAT) in presence of magnesium-ATP. The reaction was stopped by addition of EDTA, together with streptavidin-coated donor beads which bind the biotin-substrate containing any phosphorylated tyrosine residues. Anti-phosphotyrosine antibodies present on acceptor beads bind to phosphorylated substrate, thus bringing the donor & acceptor beads into close proximity. Subsequent excitation of the donor beads at 680 nm generated singlet oxygen species that interact with a chemiluminescer on the acceptor beads, leading to light emission at 520-620 nm. The signal intensity is directly proportional to the level of substrate phosphorylation and thus inhibition is measured by a decrease in signal.

Test compounds were prepared as 10 mM stock solutions in DMSO (Sigma-Aldrich Company Ltd, Gillingham, Dorset SP8 4XT Catalogue No. 154938) and serially diluted with 5% DMSO to give a range of test concentrations at 6× the required final concentration. A 2 μl aliquot of each compound dilution was transferred to appropriate wells of low volume white 384-well assay plates (Greiner, Stroudwater Business Park, Stonehouse, Gloucestershire, GL10 3SX, Cat No. 784075) in duplicate. Each plate also contained control wells: maximum signal was created using wells containing 2 μl of 5% DMSO, and minimum signal corresponding to 100% inhibition were created using wells containing 2 μl of 0.5M EDTA (Sigma-Aldrich Company Ltd, Catalogue No. E7889).

For the assay, in addition to the compound or control, each well of the assay plate contained; 10 μl of assay mix containing final buffer (10 mM Tris, 100 μM EGTA, 10 mM magnesium acetate, 4 μM ATP, 500 μM DTT, 1 mg/ml BSA), 0.5 ng of recombinant active EphA2 (amino acids 591-976; Swiss-Prot Acc. No. P29317) (ProQinase GmbH, Breisacher Str. 117, D-79106 Freiburg, Germany, Catalogue No 0368-0000-1) and 5 nM of the poly-GAT substrate (CisBio International, BP 84175, 30204 Bagnols/Cèze Cedex, France, Catalogue No. 61 GATBLB). Assay plates were then incubated at room temperature for 1 hour.

The reaction was stopped by addition of 5 μl/well stop buffer (10 mM Tris, 495 mM EDTA, 1 mg/ml BSA) containing 0.25 ng each of AlphaScreen anti-phosphoTyrosine-100 acceptor beads and streptavidin-coated donor beads (Perkin Elmer, Catalogue No 6760620M). The plates were sealed under natural lighting conditions, wrapped in aluminium foil and incubated in the dark for a further 20 hours.

The resulting assay signal was determined on the Perkin Elmer EnVision plate reader. The minimum value was subtracted from all values, and the signal plotted against compound concentration to generate $IC_{50}$ data. Examples 9 and 10 of the invention were tested in the in vitro EphA2 enzyme assay and the $IC_{50}$ values so obtained were 0.131 and 0.566 μM respectively.

The invention claimed is:
1. A compound of formula (I)

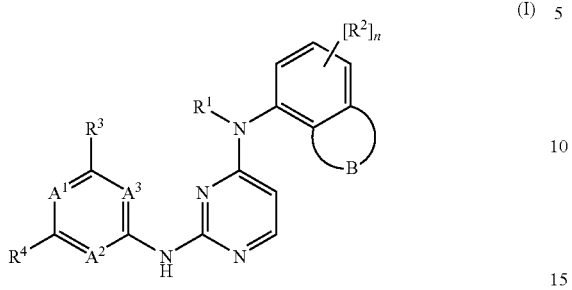

where one of $A^1$, $A^2$ or $A^3$ is N, and the others are independently selected from CH or N;

$R^1$ is hydrogen or a (1-4C)alkyl group which is optionally substituted by one or more substituent groups selected from —$OR^5$ (wherein $R^5$ is selected from hydrogen or (1-2C)alkyl), cyano, halo, or —$NR^6R^7$ (where $R^6$ and $R^7$ are independently selected from hydrogen, (1-2C)alkyl or (1-2C)alkanoyl);

ring B is a fused 5 or 6-membered carbocyclic or heterocyclic ring which is optionally substituted on a carbon atom by one or more halo groups or $C_{1-6}$alkyl groups, and where any nitrogen atoms in the ring are optionally substituted by a $C_{1-6}$alkyl or $C_{1-6}$alkylcarbonyl;

n is 0, 1, 2 or 3 and each group $R^2$ is independently selected from halogeno, trifluoromethyl, cyano, nitro or a group of sub-formula (I):

where $X^1$ is selected from a direct bond or O, S, SO, $SO_2$, $OSO_2$, $NR^{13}$, CO, CH($OR^{13}$), $CONR^{13}$, $N(R^{13})CO$, $SO_2N(R^{13})$, $N(R^{13})SO_2$, $C(R^{13})_2O$, $C(R^{13})_2S$, $C(R^{13})_2N(R^{13})$ and $N(R^{13})C(R^{13})_2$, wherein $R^{13}$ is hydrogen or $C_{1-6}$alkyl and $R^{11}$ is selected from hydrogen, $C_{1-6}$ alkyl, $C_{2-8}$alkenyl, $C_{2-8}$alkynyl, $C_{3-8}$cycloalkyl, aryl or heterocyclyl, $C_{1-6}$alkyl$C_{3-8}$cycloalkyl, $C_{1-6}$ alkylaryl or $C_{1-6}$ alkylheterocyclyl, any of which may be optionally substituted with one or more groups selected from halogeno, trifluoromethyl, cyano, nitro, hydroxy, amino, carboxy, carbamoyl, $C_{1-6}$alkoxy, $C_{2-6}$alkenyoxyl, $C_{2-6}$alkynyloxy, $C_{1-6}$alkylthio, $C_{1-6}$alkylsulphinyl, $C_{1-6}$alkylsulphonyl, $C_{1-16}$alkylamino, di-($C_{1-16}$alkyl)amino, $C_{1-16}$alkoxycarbonyl, N—$C_{1-6}$alkylcarbamoyl, N,N-di-($C_{1-6}$alkyl)carbamoyl, $C_{2-6}$alkanoyl, $C_{2-6}$alkanoyloxy, $C_{2-6}$alkanoylamino, N—$C_{1-6}$alkyl-$C_{2-6}$alkanoylamino, $C_{3-6}$alkenoylamino, N—$C_{1-6}$alkyl-$C_{3-6}$alkenoylamino, $C_{3-6}$alkynoylamino, N—$C_{1-6}$alkyl-$C_{3-6}$alkynoylamino, N—$C_{1-6}$alkylsulphamoyl, N,N-di-($C_{1-6}$alkyl)sulphamoyl, $C_{1-16}$alkanesulphonylamino and N—$C_{1-16}$alkyl-$C_{1-6}$alkanesulphonylamino, any heterocyclyl group within $R^{11}$ optionally bears 1 or 2 oxo or thioxo substituents;

$R^3$ is selected from:
(i) hydrogen, halo, nitro, cyano, or hydroxy;
(ii) an optionally substituted (1-6C)alkyl, (2-6C)alkenyl, or (2-6C)alkynyl group wherein the optional substituents are selected from: cyano; halo;
a group of sub-formula:

wherein W is selected from —O—, —S(O)$_p$— (where p is 0, 1 or 2), —CO—, —NR$^b$CO—, —CONR$^b$—, —NR$^b$CONR$^b$—, —SO$_2$NR$^b$—, —NR$^b$SO$_2$—, or —NR$^b$COO—;

$R^b$ is selected from hydrogen or (1-2C)alkyl;
and $R^9$ is selected from hydrogen or (1-4C)alkyl;
or —$NR^{10}R^{10a}$, where $R^{10}$ and $R^{10a}$ are independently selected from hydrogen, or (1-2C)alkyl, or $R^{10}$ and $R^{10a}$ are linked to form a 4, 5, 6 or 7 membered heterocyclic ring which optionally comprises, in addition to the nitrogen atom to which $R^{10}$ and $R^{10a}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C) alkyl, hydroxy(1-4C)alkyl, (1-2C)alkoxy-(1-4C) alkyl, or (1-4C)alkanoyl;

(iii) a group —$NR^{12}R^{12a}$, wherein $R^{12}$ and $R^{12a}$ are each independently selected from hydrogen or (1-6C)alkyl, or $R^{12}$ and $R^{12a}$ are linked to form a 4, 5, 6 or 7-membered heterocyclic ring which optionally comprises, in addition to the nitrogen atom to which $R^{12}$ and $R^{12a}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C) alkyl, hydroxy(1-4C)alkyl, (1-2C)alkoxy-(1-4C) alkyl, or (1-4C)alkanoyl;

(iv) a group of formula (II):

wherein X is selected from —O—, —S(O)$_p$— (where p is 0, 1 or 2), —CO—, —NR$^c$CO—, —CONR$^c$—, —NR$^c$COO—, and —NR$^c$SO$_2$—,
where $R^c$ is selected hydrogen or (1-2C)alkyl;
$R^{14}$ is a (1-4C)alkyl group which is optionally substituted by halo, hydroxy, cyano, (1-4C)alkoxy, or $R^{14}$ is

where $R^{15}$ and $R^{16}$ are independently selected from hydrogen, (1-2C)alkanoyl or (1-2C)alkyl, or $R^{15}$ and $R^{16}$ are linked to form a 4, 5, 6 or 7-membered heterocyclic ring which optionally comprises, in addition to the nitrogen atom to which $R^{15}$ and $R^{16}$ are attached, one or two further heteroatoms selected from O, N or S, and wherein any S atoms that are present may be optionally oxidised to form an SO and $SO_2$ group, and wherein any carbon atom present in the ring is optionally substituted by oxo, halo, hydroxy, cyano, (1-4C)alkyl, hydroxy (1-4C)alkyl, (1-4C)alkoxy, (1-2C)alkoxy-(1-4C) alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom is optionally substituted by (1-4C) alkyl, hydroxy(1-4C)alkyl, (1-2C)alkoxy-(1-4C) alkyl, or (1-4C)alkanoyl; or (v) a 4-7 membered heterocyclic group which is linked via a carbon atom; and R⁴ is a group —NR¹⁷R¹⁸, wherein R¹⁷ and R¹⁸ are linked to form a 4, 5, 6 or 7 membered heterocyclic ring which optionally comprises, in addition to the nitrogen atom to which R¹⁷ and R¹⁸ are attached, one or two further heteroatoms selected from O, N or S, and wherein any S atoms that are present may be optionally oxidised to form an SO or SO₂ group, and wherein any carbon atom present in the ring is optionally substituted by oxo, halo, hydroxy, cyano, (1-4C)alkyl, hydroxy(1-4C)alkyl, (1-4C)alkoxy, (1-2C)alkoxy-(1-4C)alkyl, (1-4C)alkanoyl, (1-4C)alkanesulfonyl, (1-4C)alkoxycarbonyl, (1-6C)alkylaminocarbonyl or di-(1-6C)alkylaminocarbonyl and any available nitrogen atom present in the ring is optionally substituted by (1-4C)alkyl, hydroxy(1-4C)alkyl, (1-2C)alkoxy-(1-4C)alkyl, or (1-4C)alkanoyl; or a pharmaceutically acceptable salt thereof.

2. A compound according to claim 1 wherein B is selected from OCH₂O—, —OCF₂O—, —CH═CH—NR²⁰— or —NR²⁰—CH═CH—, —O—N═CH—, —CH═N—O—, —O—NR²⁰—CH₂—, —CH₂—NR²⁰—O—, —NR²⁰—N═CH—, —CH═N—NR²⁰—, —NR²⁰—NR²⁰—CH₂— or —CH₂—NR²⁰—NR²⁰ where each R²⁰ is independently selected from hydrogen, C₁₋₆alkyl or C₁₋₆alkylcarbonyl.

3. A compound according to claim 2 wherein B is —NR²⁰—N═CH—, —CH═N—NR²⁰— or —OCH₂O—.

4. A compound according to claim 3 wherein the compound is a compound of formula (IB) or (IC)

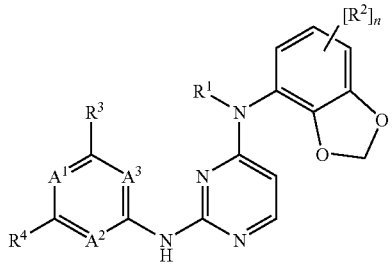

(IB)

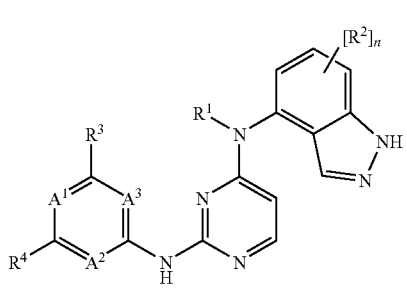

(IC)

where A¹, A², R¹, R², R³, R⁴ and n are as defined in claim 1.

5. A compound according to claim 1 wherein R¹ is hydrogen or methyl.

6. A compound according to claim 1 wherein R⁴ is a group of formula:

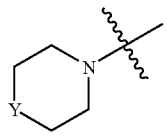

wherein Y is selected from O, NRʸ, or CRᶻ, where Rʸ is selected from hydrogen or (1-2C)alkyl, and Rᶻ is selected from hydrogen or hydroxy.

7. A compound according to claim 1 wherein R³ is a group —NR¹²R¹²ᵃ, wherein R¹² and R¹²ᵃ are each independently selected from hydrogen or (1-6C)alkyl, or R¹² and R¹²ᵃ are linked to form a 5, 6 or 7-membered heterocyclic ring, and wherein, in addition to the nitrogen atom to which R¹² and R¹²ᵃ are attached, the ring optionally comprises one or two further heteroatoms selected from O, N or S, and wherein the ring is optionally substituted on any available carbon atom by one or two substituent groups selected from oxo, halo, hydroxy, cyano, (1-4C)alkyl, or (1-4C)alkanesulfonyl, and any available nitrogen atom present in the ring is optionally substituted by (1-4C)alkyl or (1-4C)alkanoyl.

8. A compound according to claim 1 wherein n is 0 or 1, and when n is 1, R² is selected from halogeno, trifluoromethyl, cyano, hydroxy, C₁₋₆alkyl, C₂₋₈alkenyl, C₂₋₈alkynyl and C₁₋₆alkoxy.

9. A compound according to claim 1 wherein A¹ is nitrogen.

10. A compound according to claim 1 which is selected from:

N4-(5-chlorobenzo[d][1,3]dioxol-4-yl)-N2-(2,6-dimorpholinopyridin-4-yl)pyrimidine-2,4-diamine;

N4-(5-chlorobenzo[d][1,3]dioxol-4-yl)-N2-(2,6-dimorpholinopyridin-4-yl)-N4-methylpyrimidine-2,4-diamine;

N2-(2,6-dimorpholinopyridin-4-yl)-N4-(1H-indazol-4-yl)pyrimidine-2,4-diamine;

N'-(1H-indazol-4-yl)-N'-methyl-N-(2-morpholin-4-ylpyridin-4-yl)pyrimidine-2,4-diamine;

N-(2,6-dimorpholin-4-ylpyridin-4-yl)-N'-(1H-indazol-4-yl)-N'-methyl-pyrimidine-2,4-diamine;

N-(4-chloro-6-morpholin-4-yl-pyridin-2-yl)-N'-(1H-indazol-4-yl)-N'-methyl-pyrimidine-2,4-diamine;

N-(2,6-dimorpholin-4-ylpyrimidin-4-yl)-N'-(1H-indazol-4-yl)-N'-methyl-pyrimidine-2,4-diamine;

N-(2-chloro-6-morpholin-4-yl-pyridin-4-yl)-N'-(1H-indazol-4-yl)-N'-methyl-pyrimidine-2,4-diamine;

N'-(5-chloro-1,3-benzodioxol-4-yl)-N-(4-morpholino-2-pyridyl)pyrimidine-2,4-diamine;

N'-(5-chloro-1,3-benzodioxol-4-yl)-N-(6-morpholino-2-pyridyl)pyrimidine-2,4-diamine;

N-(4,6-dimorpholin-4-ylpyrimidin-2-yl)-N'-(1H-indazol-4-yl)-N'-methyl-pyrimidine-2,4-diamine; or N'-(5-chloro-1,3-benzodioxol-4-yl)-N-[2-methyl-6-(4-methylpiperazin-1-yl)pyrimidin-4-yl]pyrimidine-2,4-diamine, or a pharmaceutically acceptable salt thereof.

11. A pharmaceutical composition comprising a compound according to claim 1 in combination with a pharmaceutically acceptable carrier or diluent.

12. A process for preparing a compound of formula (I) which comprises either (A) reacting a compound of formula (II):

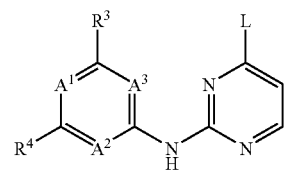

(II)

where A¹, A², A³, R³ and R⁴ is as defined in relation to formula I with the proviso that any functional groups are optionally protected, and L is a leaving group, with a compound of formula (III)

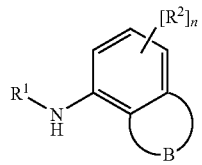
(III)

where B, $R^1$, n and $R^2$ are as defined in relation to formula I provided that any functional groups are optionally protected; or (B) by reacting a compound of formula (VII)

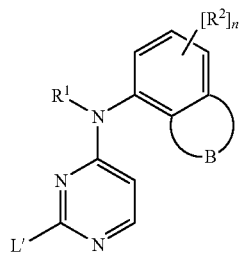
(VII)

where B, $R^1$, n, and $R^2$ are as defined in claim 1 provided that any functional groups can be optionally protected, and L' is a leaving group, with a compound of formula (VI)

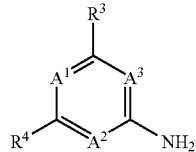
(VI)

where $A^1$, $A^2$, $A^3$, $R^3$ and $R^4$ are as defined in claim 1; or (C) reacting a compound of formula (XI)

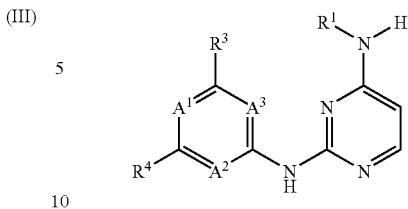
(XI)

wherein $A^1$, $A^2$, $A^3$, $R^1$, $R^3$ and $R^4$ are as defined above in claim 1;

with a compound of formula (XII)

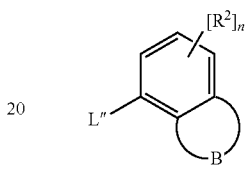
(XII)

wherein B, $R^2$ and n are as defined above in claim 1 and L" is halogen, where any functional groups are protected as necessary.

13. A compound according to claim 1 for use in the inhibition of an EphB4 or EphA2.

14. A method of inhibiting EphB4 or EphA2 in a human or animal in need thereof, which method comprises administration of an effective amount of a compound according to claim 1.

* * * * *